United States Patent [19]

Oswald et al.

[11] Patent Number: 4,528,404
[45] Date of Patent: Jul. 9, 1985

[54] HIGH TEMPERATURE HYDROFORMYLATION IN THE PRESENCE OF TRIARYLPHOSPHINE RHODIUM CARBONYL HYDRIDE COMPLEX CATALYST SYSTEMS

[75] Inventors: Alexis A. Oswald, Mountainside; Joseph S. Merola, Scotch Plains, both of N.J.; John C. Reisch, Baton Rough, La.; Rodney V. Kastrup, High Bridge, N.J.

[73] Assignee: Exxon Research and Engineering Co., Florham Park, N.J.

[21] Appl. No.: 664,037

[22] Filed: Oct. 23, 1984

Related U.S. Application Data

[63] Continuation of Ser. No. 475,809, Mar. 16, 1983, abandoned.

[51] Int. Cl.$^3$ .............................................. C07C 45/50
[52] U.S. Cl. .................... 568/454; 568/429; 568/444; 568/909
[58] Field of Search ............... 568/454, 429, 444, 909

[56] References Cited

U.S. PATENT DOCUMENTS

| | | | |
|---|---|---|---|
| 4,151,209 | 8/1979 | Paul et al. | 568/454 |
| 4,200,591 | 4/1980 | Hignett et al. | 568/454 |
| 4,200,592 | 4/1980 | Hignett et al. | 568/454 |
| 4,221,744 | 9/1980 | Unruth | 568/454 |
| 4,247,486 | 1/1981 | Brewster et al. | 568/454 |
| 4,260,828 | 4/1981 | Morrell et al. | 568/454 |
| 4,287,369 | 9/1981 | Harris et al. | 568/454 |
| 4,299,990 | 10/1981 | Tummes | 568/454 |
| 4,400,549 | 8/1983 | Richter | 568/454 |

Primary Examiner—Warren B. Lone
Attorney, Agent, or Firm—Robert J. North; E. Thomas Wheelock

[57] ABSTRACT

Certain triarylphosphine rhodium carbonyl hydride complexes $(Ar_3P)_3Rh(CO)H$ (I) and $(Ar_3P)_2Rh(CO)_2H$ (II)

are selective and stable catalysts of high temperature olefin hydroformylation. The critical factors are the maintenance of a sufficient CO partial pressure, above 25 psia, and the provision of a high excess of triarylphosphine ligand concentration, at a minimum of 1 mole per kg. To provide a high ratio of n- to i-aldehyde products of 1-olefin hydroformylation, the concentration of the tris-phosphine complex (I) is maximized. In a continuous product flashoff operation of the present process, the major high boiling solvent components are the excess phosphine ligands and monoalcohol and monoester by-products.

A combined isomerization-hydroformylation process is also disclosed for the selective conversion of internal linear olefins to terminal n-aldehydes. In this process, the concentration of the bis-phosphine complex (II) is minimized. In contrast, the concentration of the tris-phosphine complex is maximized in a process effectively converting linear internal olefins to the corresponding branched i-aldehydes.

34 Claims, 8 Drawing Figures

SCHEME OF CONTINUOUS HYDROFORMYLATION UNIT WITH CONTINUOUS PRODUCT FLASH-OFF

31P NMR STUDY OF LIGAND EXCHANGE AT VARIOUS TEMPERATURES
$(Ph_3P)_3 Rh(CO)H + 6Ph_3P$

ENERGETICS OF CATALYTIC INTERMEDIATES

CATALYTIC INTERMEDIATES IN PHOSPHINE RHODIUM COMPLEX CATALYZED HYDROFORMYLATION OF 1-BUTENE

ACS Symposia 71,503 (1981); Advances in Chemistry 196,43 (1982)

CATALYTIC PATHWAYS IN RHODIUM HYDROFORMYLATION

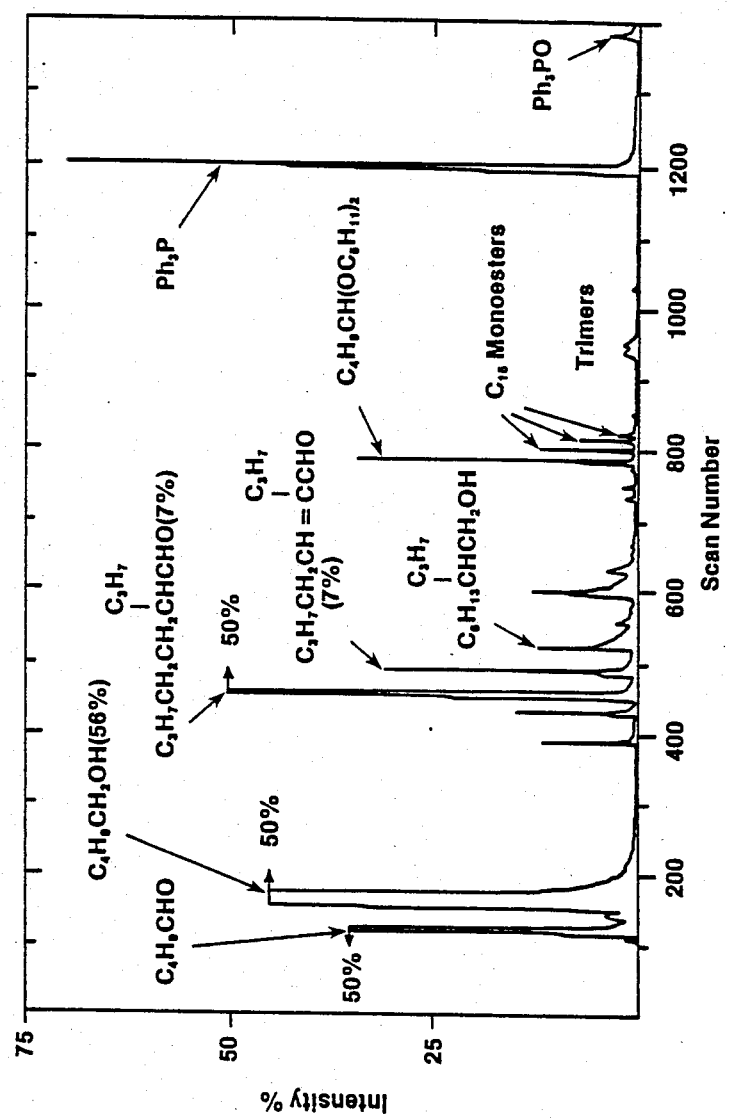

HIGH TEMPERATURE HYDROFORMYLATION IN THE PRESENCE OF TRIARYLPHOSPHINE RHODIUM CARBONYL HYDRIDE COMPLEX CATALYST SYSTEMS

This is continuation of application Ser. No. 475,809, filed 3/16/83, now abandoned.

THE FIELD OF THE INVENTION

This invention is related to a liquid phase hydroformylation process catalyzed by triarylphosphine rhodium carbonyl hydride complexes. More particularly, the improved process of the present invention converts olefinic reactants, preferably 1-n-olefins, by reacting them with CO and $H_2$ to the corresponding aldehydes, preferably n-aldehydes, in a highly selective manner. As such the selectivity of the process of the invention is dependent on favorable equilibria among the above type of catalyst complexes, in the presence of a certain large excess of triaryl or substituted triaryl phosphine ligand.

A major aspect of the invention is concerned with controlling the catalyst equilibria preferably by maximizing the concentration of the desired tris-triarylphosphine rhodium carbonyl hydride catalyst precursor complex and generating the desired selective catalyst species therefrom. The stabilization of the desired catalyst precursor by excess, free triaryl phosphine is disclosed.

A particular aspect of the present invention is an improved continuous hydroformylation of olefins via the present catalyst systems, at elevated temperatures and under increased partial pressures of CO. The continuous hydroformylation process of the present invention emphasizes the thermal and long term operational stability of the catalyst system, i.e, activity maintenance at high temperatures. For such stability the composition of the liquid reaction medium is important. As such the process of the present invention mainly relates to continuous hydroformylations in the liquid phase where the reactants are continuously fed into and the products plus unconverted reactants are continuously removed in the gas phase from the reaction mixture. Beside primary products, aldehydes, these continuous hydroformylations produce secondary by-products, monoalcohols and their monoester derivatives. The latter become high boiling solvent components. Such hydroformylations include the recirculation, in the vapor and/or liquid phase, of some or all of the reactants and of the minor quantities of excess triarylphosphine ligands, removed in the vapor phase.

The present continuous process is particularly aimed at the selective hydroformylation of 1-butene and higher olefins wherein the control of olefin isomerization side reactions is important.

Triaryl phosphine rhodium complexes are also considered as batch and continuous catalysts for a combined isomerization hydroformylation of linear internal olefins, e.g. 2-butene.

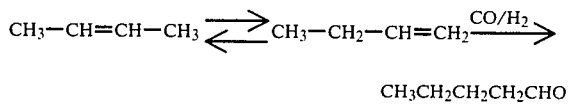

$$CH_3CH_2CH_2CH_2CHO$$

Such combined reactions allow the conversion of linear internal olefins via terminal hydroformylation to n-aldehydes.

BACKGROUND OF THE INVENTION

α-Olefin hydroformylation processes catalyzed by triaryl phosphine rhodium complex catalysts were much studied. These studies were summarized in a recent monograph on, "New Syntheses with Carbon Monoxide," edited by J. Falbe, published by Springer-Verlag, Berlin, Heidelberg, New York, 1980. See the first chapter (pages 1 to 225) on, "Hydroformylation Oxo Synthesis Roelen Reaction," by B. Cornils. Another more specific summary has been published in Vol. 17 of Advances in Organometallic Chemistry, edited by F. G. Stone and R. West, published by Academic Press, New York, N.Y., 1979. See Chapter 1 (pages 1 to 60) on "Hydroformylation," by R. L. Pruett. The catalysis chemistry of rhodium hydroformylation was recently published by A. A. Oswald et al. in the Preprints of the Petroleum Chemistry Division of the American Chemical Society (Volume 27, Part 2, pages 292 to 309, covering the symposia of the Spring National Meeting, Mar. 28–Apr. 1, 1982.

The basic patent covering the commercial hydroformylation of propylene in the presence of triarylphosphine rhodium complexes is U.S. Pat. No. 3,527,809 by R. L. Pruett and J. A. Smith. Subsequently a number of improvement patents were issued.

Most importantly, U.S. Pat. No. 4,148,830 by R. L. Pruett and J. A. Smith claims the triphenyl phosphine rhodium complex catalyzed hydroformylation of α-olefins between 50° and 145° C. in a higher boiling aldehyde condensation product as a solvent and in the presence of excess triphenyl phosphine ligand. The significance of this patent is due to the occurrence of certain side reactions, i.e. an aldol addition of the aldehyde products followed by a Tischenko type reaction as it is shown below.

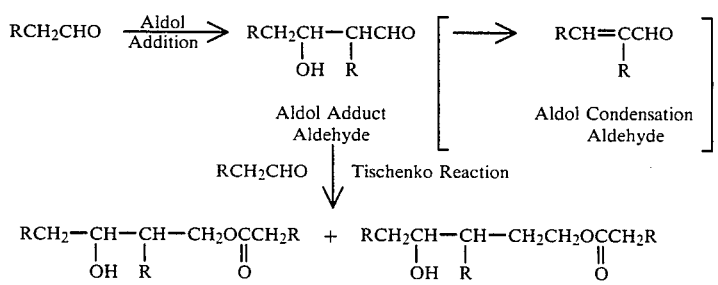

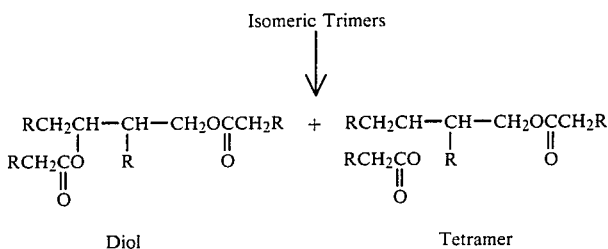

Diol          Tetramer

The so called trimer and tetramer products of these reactions are much less volatile than the main aldehyde products. Thus upon the removal of the aldehyde products in the vapor phase, these aldehyde condensation products are enriched in the liquid reaction medium and automatically provide the claimed solvent.

Based on the Pruett and Smith inventions, E. A. V. Brewester and R. L. Pruett developed a low pressure continuous product flash-off process using the triphenylphosphine rhodium complex based catalyst system in the aldehyde condensation products as solvent medium. This process is disclosed in U.S. Pat. No. 4,247,486. In this process, the olefin, CO and $H_2$ reactants plus fresh feed are recycled. Of course, an enrichment of the liquid reaction mixture in the earlier discussed higher boiling aldehyde condensation products necessarily occurs in the PFO operation disclosed by Brewester and Pruett in U.S. Pat. No. 4,247,486.

Based on the above patents, a successful, low pressure, low temperature continuous product flash-off process was commercially developed for the hydroformylation of propylene in the presence of the above triphenylphosphine rhodium complex based system (See Chemical Enginnering, page 110, Dec. 5, 1977). This process has eliminated the rhodium losses common to processes employing a chemical recovery of the catalyst. However, the known PFO catalyst system is not completely stable. Consequently, there are many patents aimed at restoring the activity of the catalyst system.

A major effort was also made on improving the catalyst activity maintenance. U.S. Pat. No. 4,227,627 by D. R. Bryant and E. Billig disclosed three critical parameters for activity maintenance in PFO hydroformylations. According to this patent, the activity maintenance, i.e. catalyst stability factor, is directly related to the triphenylphosphine to rhodium ratio and indirectly related to the CO partial pressure and temperature. These parameters were correlated to maximize the stability of the trimer solvent based catalyst system.

In the above patent, Bryant and Billig state that in a commercial operation a realistic loss of catalyst activity is 0.5% per day. They point out that using their invention this loss can be reduced to below 0.3% per day. However, as it is shown by their examples, Billig and Bryant obtained a catalyst activity loss of 2% or higher per day at 120° C. or above, due to the strong adverse effect of temperature on stability. Consequently, the Billig and Bryant process is limited to temperatures from about 90° to about 130° C.

The selectivity of the known continuous hydroformylations was expected to be adversely affected by high reaction temperatures. G. Montrasi et al. published that the amount of by-product heavy ends, specifically the "trimers," is strongly proportional to the reaction temperature. See Volume 6, pages 737 to 742 of the La Chimica e L' Industria journal in Milan, 1980.

In further improvement patents, similar low temperature processes are claimed in excess triphenyl phosphine as a solvent. U.S. Pat. No. 4,108,905 by G. Wilkinson discloses the hydroformylation of propylene and other gaseous olefins with triphenyl phosphine rhodium complexes in liquid triphenyl phosphine medium, in the absence of liquid olefin using $H_2/CO$ reactant ratios of about 2 to 0.07. Wilkinson notes that at 150° C. and above his catalyst decomposes. Wilkinson's examples included experiments with continuous product removal by distillation and analysis by gas chromatography. However, he did not observe any aldolization products. The duration of his experiments is not disclosed. A short running time would explain the apparent absence of higher boiling by products. Canadian Pat. No. 992,101 by J. H. McCracken and R. C. Williamson also discloses similar hydroformylation in triphenyl phosphine using varying $H_2/CO$ ratios but being limited to temperatures between 60° to 115° C. and batch operation.

U.S. Pat. No. 4,229,990 by H. Tummes, B. Cornils and H. Noeske describes the stabilization of triphenylphosphine rhodium complex catalysts in triphenylphosphine solvent by $C_1$ to $C_5$ paraffinic hydrocarbons employed as a component of the olefinic feed in a continuous PFO operation. According to this patent, there was a rapid decrease in catalyst activity in the absence of paraffins which acted as an extra component of the stripping gas in removing the aldehyde products. The Tummes et al. patent did not disclose the enrichment of the liquid catalyst system in aldehyde condensation products.

The decrease of the activity of the triphenylphosphine rhodium complex system was at least in part attributed to the formation of n-alkyl diphenyl phosphine ligands. See U.S. Pat. No. 4,151,209 by J. L. Paul, W. L. Pieper and L. W. Wade and U.S. Pat. No. 4,260,828 by D. G. Morrell and P. D. Sherman, Jr. and a journal article in volume 62, pages 389–394 of La Chimica e L' Industria, Milan, 1980, by G. Gregorio, G. Montrasi, M. Tampieri, P. Cavalieri d' Oro, G. Pagani and A. Andreetta. The Paul et al. patent additionally emphasized the adverse effect of even higher boiling organophosphorus by-products.

The paper by Montrasi et al. pointed out that for example in propylene hydroformylation, the formation of propyldiphenylphosphine is directly related to the propylene reactant concentration. Alternatively, inactive phosphido complexes are formed at low propylene concentration. Furthermore, triphenylphosphine is oxidized to triphenylphosphine oxide by aldehydes, particularly by 2-ethylhexenal, according to Montrasi et al. In general, the scientific literature is highly pessimistic regarding a substantially complete stabilization of the homogeneous liquid catalyst systems based on triarylphosphine rhodium complexes.

It is apparent from the prior art that 1-n-olefins are much more reactive in phosphine rhodium complex catalyzed hydroformylation than internal or vinylically substituted olefins. It was disclosed in U.S. Pat. No. 4,287,370 by N. Harris, A. J. Dennis and T. F. Shevels that a mixture of isomeric butenes can be used as a feed in a continuous PFO process using a trimer solvent for the selective conversion of the 1-butene component to n-valeraldehyde.

Attempts were also made to utilize the triphenylphosphine rhodium complex catalyst system in the conversion of $C_4$–$C_6$ internal linear olefins to the corresponding n-aldehydes via combined isomerization-hydroformylation. According to U.S. Pat. No. 4,200,592 by R. R. Hignett and P. J. Davidson only about a 0.16 ratio of n- to i-valeraldehyde products is obtained in such a process starting with 2-butene. However, Hignett et al. disclose that the n/i product ratio can be somewhat increased in the presence of added cocatalysts based on complexes of other transition metals.

In contrast to the known prior art, it was surprisingly found in the present invention that superior high temperature hydroformylation selectivity and excellent operational stability are achieved using homogeneous liquid triarylphosphine rhodium complex catalyst systems when the excess triaryl phosphine ligand is a major solvent component and a sufficient concentration of dissolved CO reactant is maintained to avoid CO starvation.

It was shown in the batch hydroformylation studies of the triphenylphosphine rhodium complex based catalyst systems that superior hydroformylation selectivities are obtained when the concentration of the excess triphenyl phosphine ligand is between 1 and 2.9 molar and when the $H_2/CO$ ratio is maintained between 2.5 and 10. In this preferred concentration range of excess ligand, the hydroformylation catalyst system is much more stable and provides a higher n- to i-ratio of aldehyde products than at the lower concentrations disclosed in the Pruett and Smith patents. Furthermore, the present catalyst system also provides a higher ratio of n/i products than the triphenyl phosphine only process of the Wilkinson patent.

In addition, it was found that the catalyst system is much less sensitive to higher partial pressures of carbon monoxide when the phosphine concentration is high. In effect, both the apparent rate of the hydroformylation and its selectivity to total aldehydes increases with increasing CO partial pressures. In contrast, the Pruett et al. and Bryant et al. patents disclose a process limited to a top CO partial pressure of 55 psia.

Surprisingly, the selectivity of the present catalyst system with regard to the n-versus i-ratio of the aldehyde products was found to be insensitive to the triaryl phosphine to rhodium ratio. Under a certain set of reaction conditions, the selectivity is essentially determined by the triaryl phosphine concentration alone. The rhodium concentration can be independently increased to achieve the desired reaction rate without affecting the n/i ratio of products.

In the continuous high temperature hydroformylation studies of various triphenylphosphine rhodium complex based catalyst systems it was surprisingly found that trimer solvent formation by Pruett et al, and Montrasi et al., can be substantially eliminated. In the continuous process of the present invention the formation of the higher molecular weight by products is suppressed. The key intermediate of the secondary higher molecular weight by-products was found to be the unsaturated aldol aldehyde rather than the hydroxy aldol aldehyde. As shown below, during the present hydroformylation process, the unsaturated aldol aldehyde by-product undergoes hydrogenation and subsequent aldolization, oxidation and esterification reactions. Consequently, the resulting monoalcohols and monoesters rather than the trimers are enriched in the liquid reaction mixture during product distillation and as such become the high boiling solvent components

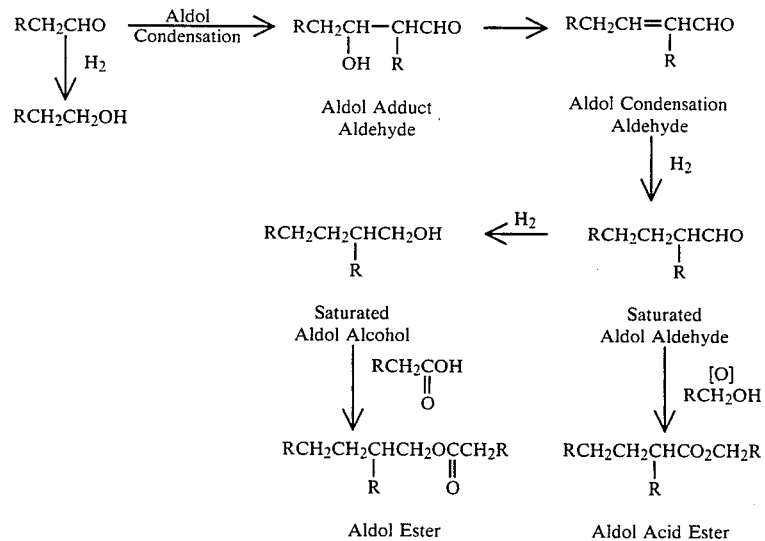

In addition, the liquid reaction media of the continuous process of the present invention contain significant amounts of dissolved olefin in the liquid phase. Thus the reaction occurs in the liquid phase. This is in contrast to the disclosures of the Wilkinson patent which specifies hydroformylation of a gaseous olefin in the absence of liquid olefin reactant. The present reaction media also contain increased amounts of dissolved CO as a result of increased CO partial pressures, in excess of 25 psia. The latter is in contrast to the minimum CO partial pressures preferred in the Pruett et al. and Bryant et al. patents.

As a result, the high temperature continuous hydroformylation process of the present invention shows a unique combination of selectivity and maintenance of catalyst activity. In contrast to the Tummes et al. and Paul et al. patents the maintenance of catalyst activity in these systems is not due to either the presence of alkanes in the feed or the absence of high boiling organophosphorus by-products in the mixture. In the present selective process for n-aldehyde production, the stability is believed to be mainly attributable to the maximization of the rhodium species present as the tris-triarylphosphine rhodium carbonyl hydride complex via the special reaction medium and the above discussed operational parameters.

As a result of the understanding of the various factors controlling the complex equilibria among the various complexes of the triarylphosphine rhodium based catalyst complexes, the present invention also provides an improved combined isomerization hydroformylation process for the selective conversion of internal olefins to n-aldehydes at minimum CO partial pressure. In contrast to the Hignett et al. patent, the present process does not require the presence of transition metals other than rhodium.

Finally, it is surprisingly found that the present high temperature process is also applicable for the selective hydroformylation of internal linear olefins to i-aldehydes, at maximum CO partial pressures.

SUMMARY OF THE INVENTION

In accordance with the present invention, it has been discovered that the high temperature stability, activity and selectivity of rhodium complexes of triphenylphosphine and the like can be improved by appropriately increasing the concentration of the excess, free triarylphosphine and the excess free CO ligands. Thus, the hydroformylation process of the present invention comprises reacting dissolved olefinic feed with CO and $H_2$ in a homogeneous liquid phase medium at temperatures between about 120° and 200° C. and at a total pressure in the range of 100 to 1500 psi to selectively produce aldehydes in the presence of tris-triarylphosphine rhodium monocarbonyl hydride and bis-triarylphosphine rhodium dicarbonyl hydride complex catalysts free from halogen on the rhodium wherein said reaction medium comprises a minimum of 1 mole per kg, i.e. $\overline{M}$, phosphorus equivalent of excess triarylphosphine ligand as a catalyst stabilizer modifier and oxygenated solvents mainly comprising free monohydric alcohols and their monocarboxylic acid esters and acetals, and branched aldehydes.

Rhodium complexes of triaryl phosphines plus excess triaryl phosphine represent an important type of catalyst system for the selective terminal hydroformylation of 1-n-olefins. Particularly, tris-triphenylphosphine rhodium carbonyl hydride plus triphenyl phosphine are components of a widely used homogeneous catalyst system for the continuous hydroformylation of propylene to provide n- rather than i-butyraldehyde:

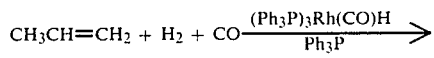

Under the conditions of the commercial process at about 100° C., the butyraldehyde products are continuously removed in the vapor phase together with the unreacted products. However, the present commercial product flash-off (PFO) process allows only limited olefin to aldehyde conversions and is not applicable to higher olefins because of the instability of the catalyst system at higher temperatures.

Hydroformylation at increased temperatures is advantageous because of the increased activity of the rhodium complex catalyst. In the continuous PFO hydroformylation the increased reaction temperature is also important because under a given set of conditions, it largely determines the amount of the aldehyde product which can be removed by distillation from the reaction mixture (FIG. 1). With an increasing carbon number of the olefin reactants, the boiling points of the corresponding aldehyde products are sharply elevated. For example, at atmospheric pressure, the boiling points of n-butyraldehyde and n-valeraldehyde are 75° and 103° C., respectively. At the superatmospheric pressures of commercial hydroformylations, there are of course corresponding elevations of the atmospheric boiling points. Consequently, although PFO hydroformylation at about 100° C. is highly applicable to n-butyraldehyde production from propylene, it does not provide similarly attractive results when employed for n-valeraldehyde production from 1-butene.

The present hydroformylation process is preferably practiced in a continuous mode of operation comprising reacting a dissolved $C_2$ to $C_{10}$ preferably a $C_4$ to $C_{10}$ olefinic feed with CO and hydrogen in the manner described. This continuous hydroformylation is additionally characterized by the continuous introduction of reactants and the continuous removal and separation of the products in the vapor phase. The product removal by a flash-off type distillation can be effected either from the reaction vessel during the reaction (PFO) or from a separate flash-off vessel, usually at a reduced pressure. The latter operation preferably comprises a continuous recycle of the reaction medium containing the nonvolatile catalyst (RFO). A PFO operation removing the products from the medium during the reaction in the gas phase is preferred over RFO, especially with volatile olefin feeds.

The present process is preferably employed for the selective production of n-aldehydes from vinylically unsubstituted terminal olefins. Thus the process preferably comprises selectively reacting a dissolved 1-n-olefin, preferably 1-butene, with CO and $H_2$ in a homogeneous liquid phase to selectively produce a n-aldehyde, preferably n-valeraldehyde, wherein the ratio of $H_2$ to CO reactant is preferably in the range of about 2.5 to 10 to assure a ratio above 10 of the n- to i-aldehyde products. To stabilize the catalyst system, avoid terminal to internal olefin isomerization and maintain catalyst activity, the concentration of excess triphenylphosphine ligand and the partial pressure of CO reactant are kept appropriately high. Thus daily loss of catalyst activity is kept below about 0.5%, preferably 0.3%.

Preferred feeds for the production of n-aldehydes from 1-olefins via the present selective process include olefin mixtures. Thus a mixture of isomeric butenes, particularly a mixture of 1-butene and 2-butene can be used as a 1-olefinic feed to selectively produce n-valeraldehyde from 1-butene. The relatively nonreactive olefin isomers of such a mixed feed mainly act as a stripping gas to remove the products.

The present process is also applicable for homogeneous combined isomerization hydroformylation comprising isomerizing an internal linear olefin, preferably 2-butene, to a terminal 1-n-olefin, preferably 1-butene, and hydroformylating the 1-n-olefin component of the resulting isomeric mixture in one operation. The overall reaction conditions of this combined process are the same as those of the direct hydroformylation. However, the partial pressure of the CO hydroformylation reactant which inhibits the isomerization step is kept at a minimum, i.e. below 100 psi, preferably below 20 psi.

Finally, the present process can be also used for the production of iso-aldehydes from linear internal olefins. In this process, the role of the excess triarylphosphine is only that of a stabilizer. The formation of n-valeraldehyde by-products is inhibited by a relatively high CO partial pressure, preferably above 100 psi most preferably above 300 psi. The increased CO partial pressure also increases the activity of the catalytic complex of this process, primarily bis-triarylphosphine rhodium dicarbonyl hydride.

BRIEF DESCRIPTION OF THE DRAWINGS

FIG. 8 shows the oxygenated solvent components of the high temperature 1-butene hydroformylation catalyst system of the present invention.

CATALYST COMPLEXES

The process of the present invention is based on a new understanding of the catalytic mechanism of hydroformylations catalyzed by triarylphosphine rhodium complexes. This understanding is the result of determining the structure and equilibria of the various catalytic rhodium complexes by $^{31}P$, $^{13}C$ and $^1H$ nuclear magnetic resonance (NMR) spectroscopy under simulated hydroformylation conditions.

Complexes derived from the starting tris-triphenylphosphine rhodium carbonyl hydride were investigated in solution in the presence of varying amounts of excess ligand and under varying pressure of $H_2$ and CO. It was shown that, dependent on the conditions, the starting tris-phosphine complex (I) was equilibrated with its bis-phosphine derivative (II)

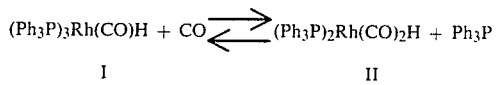

$$(Ph_3P)_3Rh(CO)H + CO \rightleftharpoons (Ph_3P)_2Rh(CO)_2H + Ph_3P$$
$$\text{I} \qquad\qquad\qquad\qquad \text{II}$$

These two complexes were the main catalyst components in rhodium hydroformylations. At low temperatures, their spectra could be clearly identified.

Figure 2:
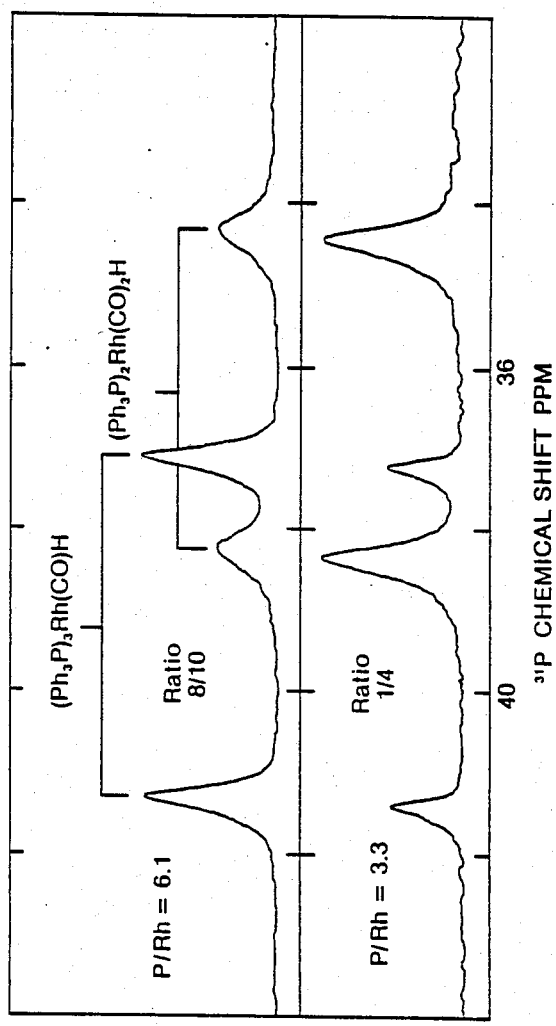
FIG. 2 illustrates, by $^{31}P$ NMR spectra, the effect of excess phosphine on the equilibrium between tris-triphenylphosphine rhodium carbonyl hydride and bis-triphenylphosphine rhodium dicarbonyl hydride.

It was found that under $H_2/CO$ pressure the tris-phosphine complex (I) was partially or completely converted to the bis-phosphine derivative (II). As it is indicated by the $^{31}P$ phosphorus spectra of FIG. 2, in the presence of excess phosphine (P/Rh=6), less bis-phosphine complex was formed than in its absence (P/Rh=3). In the presence of excess phosphine, the ratio of the overlapping doublet signals of the complexed phosphine ligands of the two complexes, I/II, equaled 8/10. In the absence of excess phosphine about 80% of the rhodium was in the form of the bis-phosphine (I/II=1/4). Similar studies were carried out at very high phosphine concentrations. In these studies, it was found that at moderate CO partial pressures most of the rhodium was present in the form of its tris-phosphine complex (I).

Figure 3:
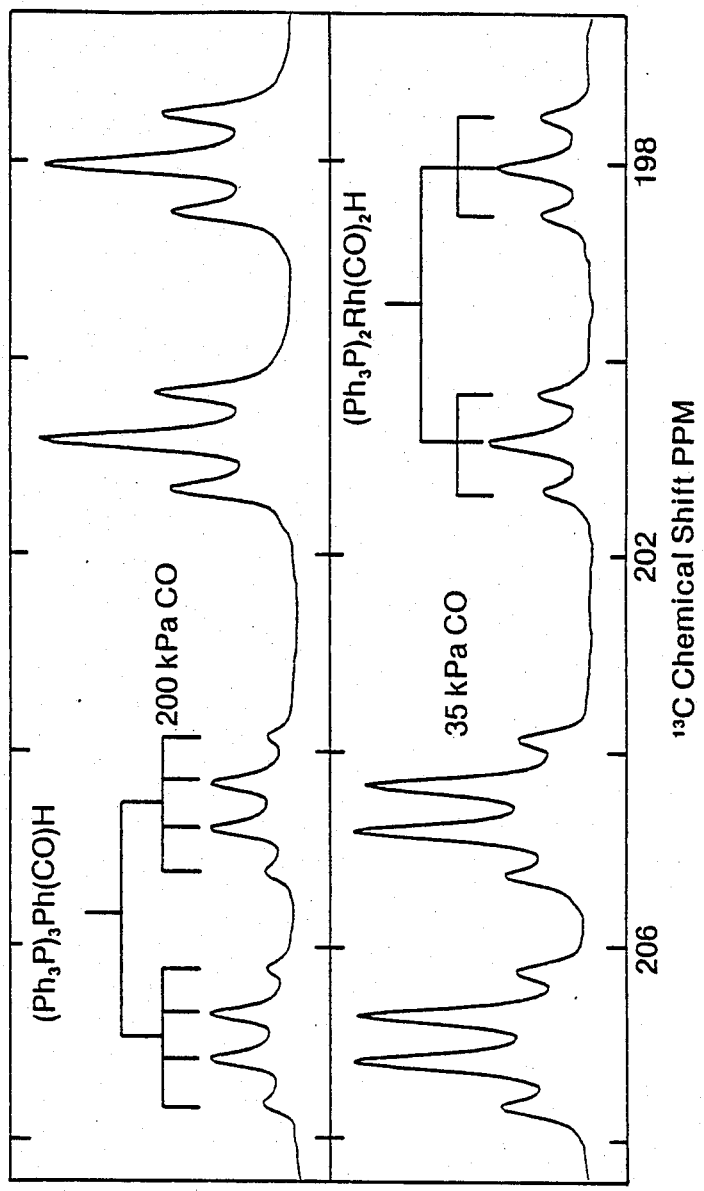
FIG. 3 illustrates, by $^{13}C$ NMR spectra, the effect of CO partial pressure on the equilibrium between tris-triphenylphosphine rhodium carbonyl hydride and bis-triphenylphosphine rhodium dicarbonyl hydride.

The effect of increased CO partial pressure was similarly studied by NMR techniques as it is indicated by FIG. 3. In this case, $^{13}C$ spectroscopy with a broader chemical shift range was used to characterize the complexed CO ligands. Thus signal overlap was avoided. Using enriched $^{13}CO$, the double quartets of the tris-phosphine complex and the double triplets of the bis-phosphine complex were clearly identified. The relative intensities of these signals exemplify that an increased partial pressure of CO results in the conversion of some of the tris-phosphine complex to the bis-phosphine complex (II).

The state of equilibrium between tris- and bis-triarylphosphine complexes, in general,

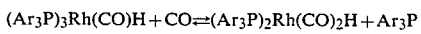

$$(Ar_3P)_3Rh(CO)H + CO \rightleftharpoons (Ar_3P)_2Rh(CO)_2H + Ar_3P$$

also depends on the structure of the triarylphosphine ligand. Sterically crowded tris-triarylphosphine complexes are comparatively readily converted to the corresponding bis-phosphine complexes because of the smaller steric requirement of the carbonyl ligand. Increased steric crowding results from the ortho-substitution of the triarylphosphine ligands.

At low temperature, neither the tris- nor the bis-phosphine complex is an effective hydroformylation catalyst. To become active, these coordinatively saturated complexes are to dissociate to provide highly reactive coordinatively unsaturated species. These dissociation reactions leading to catalyst activation are temperature dependent and reversible.

Figure 4:
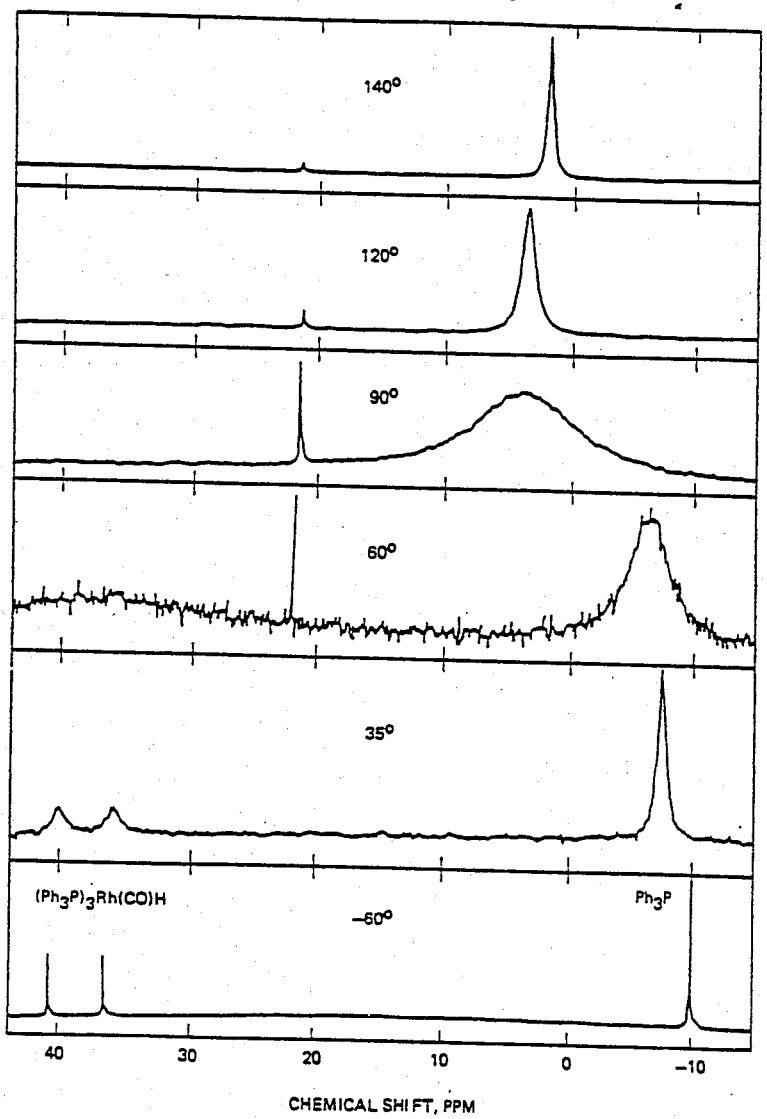
FIG. 4 illustrates the temperature dependence of the reversible dissociation of tris-triphenylphosphine rhodium carbonyl hydride by the variable line shape of $^{31}P$ NMR signals.

The dissociation of the remarkably stable tris-triphenylphosphine complex at various temperatures was studied in detail by $^{31}$P NMR. These studies are indicated by FIG. 4. A selective, highly reversible dissociation of the phosphine ligand occurred. However, the equilibrium was far shifted to the side of the coordinatively saturated species, even at high temperatures

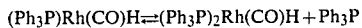

Figure 5:
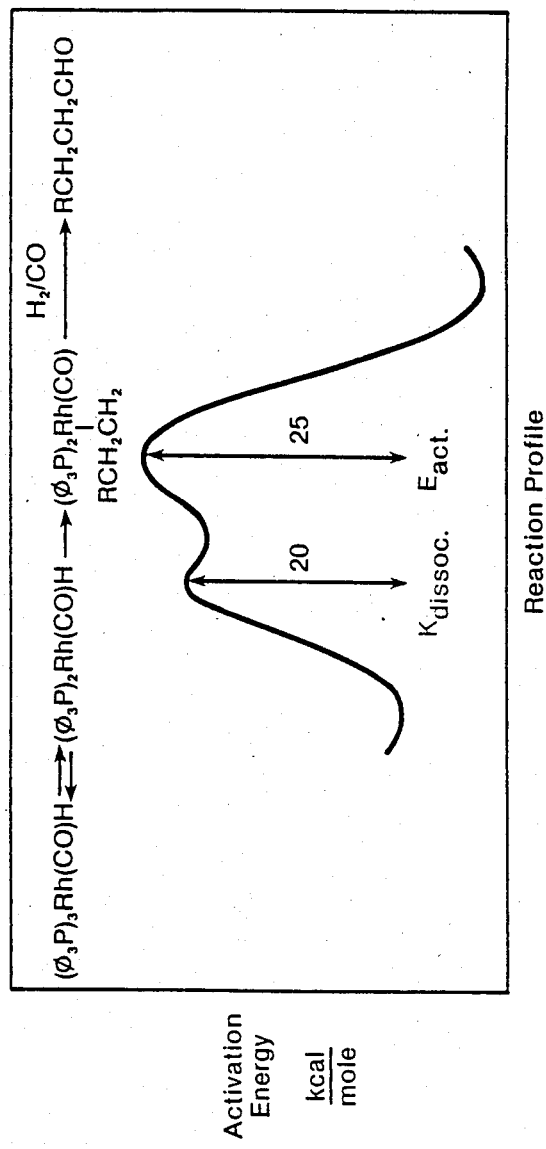
FIG. 5 outlines the reaction profile of the triphenylphosphine rhodium carbonyl complex intermediates of olefin hydroformylation and thus shows the energetics of these catalytic intermediates.

Thus the doublet signals of the complexed phosphorus were due to the trisphosphine complex. An increasing line broadening of these signals between $-60°$ and $+60°$ C. indicated an increasing rate of dissocation. At even higher temperatures, dissociation became faster. This resulted in a single composite signal for both complexed and free phosphines. With increasing temperature, i.e. ligand exchange, this composite signal became increasingly sharp. Dissociation rates could be determined via line shape analysis. The activation energy of dissociation $k_{dissoc}$ was found to be about 20 Kcal, somewhat less than that of hydroformylation. The reaction of the coordinatively unsaturated complex with the olefin apparently involves a transition state of higher energy, as indicated by FIG. 5.

Thus the dissociation of the coordinately saturated trisphosphine complex was found to be a necessary but insufficient condition for hydroformylation. The concentration of the reactive coordinatively unsaturated species is directly related to the temperature but inversely affected by the excess ligand. Thus the thermal stability of the catalyst system is directly proportional to the excess ligand.

The dissociation of tris-triarylphosphine rhodium carbonyl hydride complexes and thus their catalytic activity depend not only on the temperature but on the structure of the triarylphosphine ligand. For example, sterically crowded tris-phosphine complexes containing orthosubstituted triarylphosphines exhibit accelerated rates of dissociation and thus increased activity.

In contrast to the tris-phosphine complex, the bis-phosphine complex was found to undergo a nonselective dissociation indicated by the exchange of both the phosphine and CO ligands:

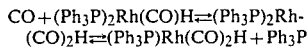

Figure 6:
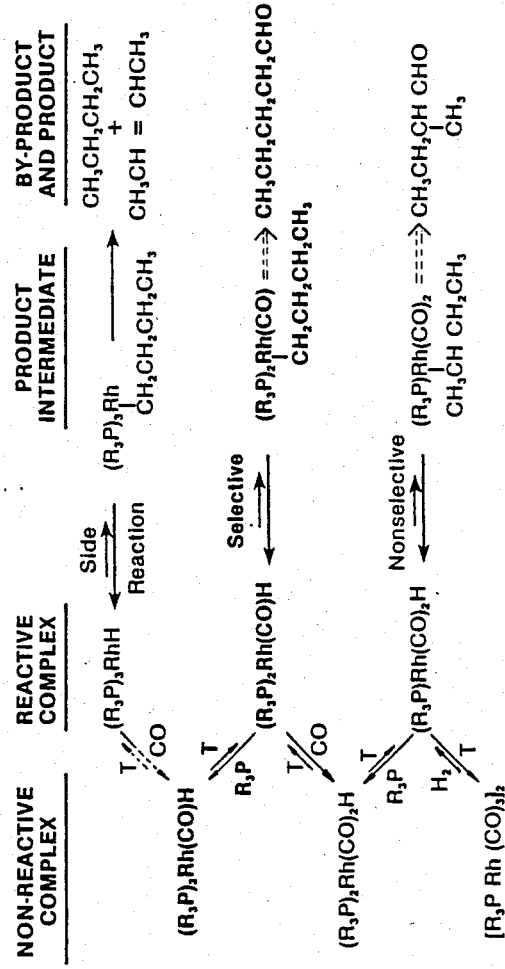
FIG. 6 shows the multiple equilibria among the triarylphosphine rhodium complex intermediates of 1-butene hydroformylation and their role in the formation of n- and/or i-valeraldehyde products, and butane and 2-butane by-products.

The NMR spectroscopic studies were correlated with the results of various catalytic studies. Correlation of the results led to the identification of the catalytic intermediates. For 1-butene hydroformylation, these intermediates are shown by FIG. 6. As it is indicated by the left side of this figure, the major coordinatively saturated species in these systems are the tris-phosphine rhodium monocarbonyl hydride and the corresponding bis-phosphine dicarbonyl hydride. In the case of selective hydroformylations in the presence of a large excess of phosphine and reduced carbon monoxide concentration, the main species in solution is the tris-phosphine monocarbonyl hydride. Some of this complex dissociates to give the corresponding trans-bis-phosphine carbonyl hydride, which in turn reacts with the olefins to form the normal alkyl derivative. The latter then reacts with CO and rearranges to a stable acyl rhodium derivative which leads to the n-aldehyde product. Similar dissociation followed by olefin reaction forms the secondary alkyl derivative which leads to the isoaldehyde, in both cases by well established sequence of reactions. Finally, it is shown by the top of the scheme that trace amounts of a carbonyl free tris-phosphine hydride can be responsible for the formation of some of the alkane and internal butene by-products via alkyl rhodium intermediates.

Figure 7:
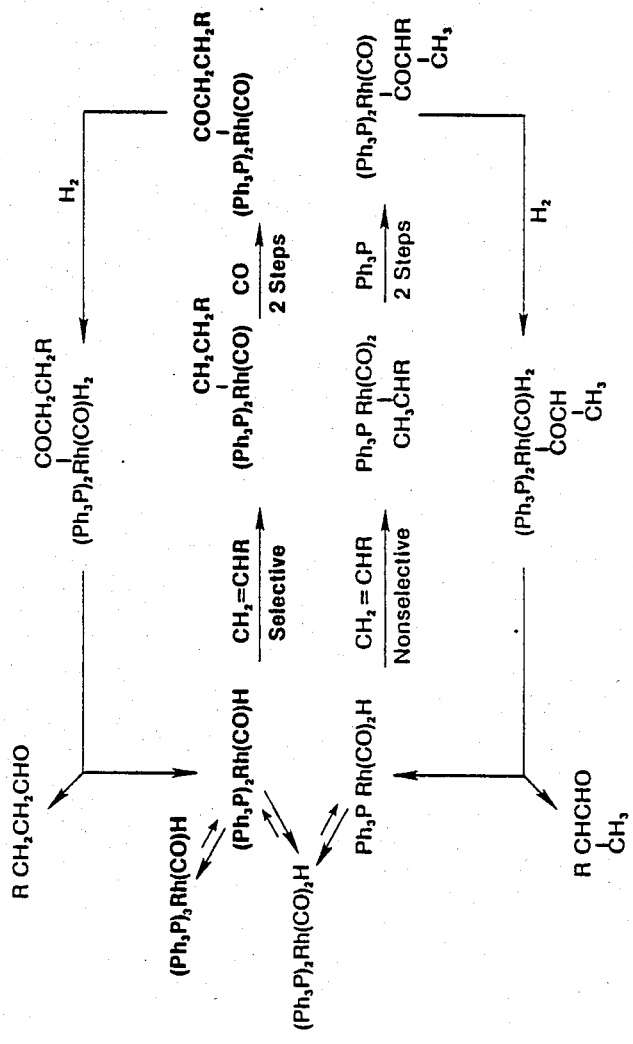
FIG. 7 outlines the alternate catalytic pathways of triarylphosphine rhodium complex catalyzed hydroformylation. Dependent on the carbonylation degree of the active complex species, these pathways lead to n- or n- plus i-aldehyde products of 1-n-olefin hydroformylation.

Putting these equilibria together with a known sequence of subsequent reactions, two catalytic cycles for selective nonselective hydroformylation can be visualized, respectively, as it is shown by FIG. 7. In the selective cycle, the key intermediate is a bis-phosphine monocarbonyl hydride which is converted to the alkyl rhodium derivative. This compound then picks up CO and forms the well known acyl rhodium complex, which undergoes oxidative hydrogen addition to form the dihydride. The dihydride extrudes the normal aldehyde, the desired product, and regenerates the coordinatively unsaturated species. A similar catalytic cycle involving a dicarbonyl hydride was found for nonselective hydroformylation as indicated by FIG. 7.

The above understanding of selective and nonselective hydroformylation reactions can be summarized by stating that the tris-phosphine monocarbonyl hydride is the main catalyst proposed for selective hydroformylation to provide n-aldehydes. Reactions occur on dissociation of this species. Multiple equilibria are involved, and understanding these equilibria allows us to control the selectivity of such reactions to either produce a maximum amount of total aldehydes or a maximum ratio of normal-isoproducts.

Thus the importance of the monocarbonyl rather than dicarbonyl hydride intermediates is found in selective hydroformylation to provide a high n/i ratio of aldehydes. This is in contrast with the associative and dissociative mechanisms suggested by the early Wilinson publications particularly with the paper in the Journal of Chemical Society A, pages 3134 to 3142 in 1968 by D. Evans, J. A. Osborn and G. Wilkinson.

As suggested by the equilibria and supported by the catalytic experiments, the relative amounts of the two coordinatively unsaturated complexes leading to different hydroformylation pathways can be controlled by the excess Ph$_3$P and CO concentrations. The above discussed active carbonyl hydride and inactive carbonyl dimer complexes are in·an equilibrium. At increased temperatures, the control of the intermediates becomes more difficult due to their decreased stability. A high concentration of Ph$_3$P was essential for maintaining the stability of the overall catalyst system e.g. by increasing the concentration of the tris-phosphine complex which acts as a stable reversible reservoir of the active species. An increase of CO partial pressure was found to be surprisingly important at high temperature for avoiding excessive paraffin formation by hydrogenolysis via the alkylrhodium intermediate and an analogous formation of 2-olefin isomers by elimination from a secondary alkylrhodium complex. This also helps to explain the direct CO dependence observed on the rate in the high temperature region.

The triarylphosphine rhodium complex based homogeneous liquid catalyst systems contain the catalytic rhodium carbonyl hydride complexes and excess triaryl phosphine ligands plus oxygenated solvents. Together with the dissolved synthesis gas reactant these compositions constitute an essentially complete reaction medium.

The catalyst compositions of the present invention are mainly defined as coordinatively saturated tris- and/or bis-triarylphosphine rhodium carbonyl hydride complexes. On phosphine and CO dissociation, these major complexes provide minute concentrations of the active species already discussed.

The triaryl phosphine rhodium complex catalyst components are preferably of the formula

[Ar$_2$P)$_y$Q$^y$]$_g$Rh(CO)$_2$H wherein Ar is aryl, preferably an independently selected C$_5$ to C$_{18}$, preferably C$_6$ to C$_{12}$, unsubstituted or substituted aryl, preferably phenyl. The number of aryl and phenyl substituents is 1 to 3, preferably 1. The preferred position of phenyl substituents is para- or meta. In the case of internal linear olefin reactants ortho-substituted ligands are preferred. The substituents are selected with the proviso that they must exclude groups which are reactive or chemically unstable under hydroformylation conditions. The preferred substituents are selected from the group consisting of hydrocarbyl, preferably alkyl, hydrocarbyloxy, cyano, nitro, hydrocarbylthio, hydrocarbylsulfonyl, hydrocarbylamino, hydrocarbylamido, halo and fluoroalkyl groups. More preferred are hydrocarbyl particularly alkyl groups.

The meaning of the Q groups of the above formula is aryl or arylene. The aryl group is as defined for the symbol Ar. The arylene group is a C$_5$ to C$_{18}$, preferably C$_6$-C$_{12}$, unsubstituted or substituted arylene more preferably phenylene, most preferably p-phenylene. The arylene substituents are selected with the priviso excluding reactive groups. Alkyl substituents are preferred. The arylene group is preferably unsubstituted. It is preferred that one of the Ar and Q groups be different.

The symbol y indicates that valency of the Q groups; y is 1 or 2. If Q is aryl, y is 1; if Q is arylene, y is 2. The symbol g means 1 to 3, preferably 2 or 3, more preferably 3. The symbol z is 1 or 2, preferably 1.

A preferred type catalyst complex is of the formula

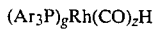

(Ar$_3$P)$_g$Rh(CO)$_z$H wherein meaning of the symbols is the same.

Another preferred type catalyst complex, derived from arylene bis-phosphines, is of the following formula

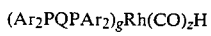

(Ar$_2$PQPAr$_2$)$_g$Rh(CO)$_z$H wherein Q is arylene and the rest of the symbols are as previously defined.

The above types of catalysts are preferably of the formula

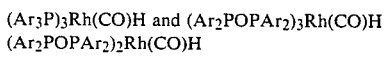

(Ar$_3$P)$_3$Rh(CO)H and (Ar$_2$POPAr$_2$)$_3$Rh(CO)H
(Ar$_2$POPAr$_2$)$_2$Rh(CO)H Other types of catalysts are of the following formula

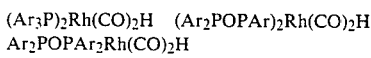

(Ar$_3$P)$_2$Rh(CO)$_2$H  (Ar$_2$POPAr)$_2$Rh(CO)$_2$H
Ar$_2$POPAr$_2$Rh(CO)$_2$H

As indicated by the above formula the arylene bis-phosphine complexes include both chelated and non-chelated compounds. The chelated bis-phosphine complexes of cis- rather than trans-stereochemistry, e.g.

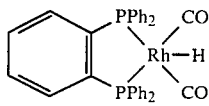

lead to particularly low n/i ratios.

Examples of the aryl groups are phenyl, fluorophenyl, difluorophenyl, tolyl, xylyl, benzoyloxphenyl, carboethoxyphenyl, acetylphenyl, ethoxyphenyl, phenoxyphenyl, biphenyl, napthyl, hydroxyphenyl, carboxyphenyl, trifluoromethylphenyl, tetrahydronaphthyl, furyl, pyrryl, methoxyethylphenyl, acetamidophenyl, dimethylcarbamylphenyl, chlorophenyl, t-butylphenyl.

Examples of the arylene groups are phenylene, naphthylene, biphenylene, methylene bis-phenyl, oxy bis-phenyl, propylidene bis-phenyl.

Examples of the substituents of the aryl and arylene groups are methyl, dodecyl, t-butyl, ethoxy, phenoxy, trifluoromethyl, acetoxy, benzoyloxy, carboethoxy, acetamido, chloro, fluoro, bromo, hydroxy, carboxy, methylthio, methylsulfonyl, trimethylsilyl.

The triarylphosphine rhodium carbonyl hydride catalyst complex compositions of the present invention include mixed ligand complexes containing one mole alkyldiarylphosphine ligand per rhodium atom. Thus the broad general formula is the following:

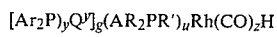

[Ar$_2$P)$_y$Q$^y$]$_g$(AR$_2$PR')$_u$Rh(CO)$_z$H wherein R' is alkyl and substituted alkyl, preferably C$_2$ to C$_{10}$ alkyl, more preferably C$_4$ to C$_{10}$ n-alkyl; g is 1 to 3; u is 0 or 1, the other symbols being as described above.

For example, such mixed ligand complexes are of the formula

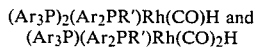

(Ar$_3$P)$_2$(Ar$_2$PR')Rh(CO)H and
(Ar$_3$P)(Ar$_2$PR')Rh(CO)$_2$H

In general, such complexes are formed during continuous hydroformylation reactions via reversible ligand displacement, e.g.

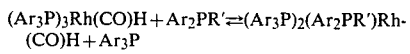

(Ar$_3$P)$_3$Rh(CO)H+Ar$_2$PR'⇌(Ar$_3$P)$_2$(Ar$_2$PR')Rh-(CO)H+Ar$_3$P

The Ar$_2$PR' reactants of such displacement reactions are continuously formed in trace quantities during hydroformylation. For example, in case of continuous 1-butene hydroformylation, n-butyldiphenylphosphine and n-amyldiphenyl phosphine are formed. The carbon numbers of the alkyl groups of such ligands apparently correspond to that of the olefin reactant and main aldehyde product, respectively.

In contrast to the previously discussed prior art processes of Paul et al., Morrell et al. and Gregorio et al., the formation of trace quantities of alkyldiarylphosphine ligands and their rhodium complexes of the above formula has no significant adverse effect on the present process. Due to the high temperature of the present process most of the free alkyldiarylphosphine ligand is usually effectively stripped. Also, the mixed ligand complexes have comparable activities to the pure triarylphosphine complexes. In effect, the presence of mixed ligand complexes can be advantageous due to the increased total aldehyde selectivity.

The mixed ligand complexes of the present invention are outside the scope of the inventions of copending applications of Ser. No. 120,971 and Ser. No. 295,193 by Oswald et al. filed on Feb. 12, 1979 and Aug. 21, 1981, respectively. The phosphine rhodium complex based catalyst systems of the process of the earlier application are primarily alkyldiarylphosphine rather than triarylphosphine ligand based and they are not distinguished by the presence of carboxylic acid monoester and free alcohol solvent components.

While the concentration of the catalytic rhodium complex obviously affects the hydroformylation, there is no critical catalyst concentration in the present process. In general, the catalyst concentration employed is sufficient to assure the desired rate. The concentration of the catalyst is best described on a rhodium basis. The concentration is usually between about 0.1 and 1000 $m\bar{M}$ preferably 1 and 100 mM rhodium complex in the liquid reaction medium. The latter is in the range of 100 ppm and 10,000 ppm. Since the hydroformylation rate is directly related to the olefin concentration by a first order dependency, lower rhodium concentrations are sufficient at high olefin concentrations. Conversely, higher rhodium concentrations are required at increased excess triarylphosphine concentration due to an inverse rate dependency on the phosphine concentration.

In contrast to the prior art, the selection of rhodium concentration is not influenced by a desired phosphine to rhodium ratio. Under the conditions of the present process, the P/Rh ratio has no significant effect on the n/i ratio of the aldehyde products. In general, the rhodium concentrations employed are higher than those disclosed by the prior art.

As a consequence of the high rhodium concentrations, the P/Rh ratios are generally relatively low in the present process, even though the absolute phosphine ligand concentration is high. Ligand to rhodium ratios in the range of 10 to 3000, preferably 100 to 1000 are typical.

FREE TRIARYLPHOSPHINE LIGANDS

The free triaryl phosphine components of the present catalyst system are preferably of the same structure as those triaryl phosphine ligands which are complexed to the rhodium.

$(Ar_2P)_yQ_y$

The meaning of the symbols in the above phosphine formula is as previously described.

A preferred group of triaryl phosphines is liquid at ambient temperature. Another preferred group possesses unsymmetrical structures. The boiling point of a preferred group is greater than 400° C. A further preferred group, has melting points from about 50° to 150° C. and can be crystallized from the catalyst system. Finally, a preferred group is represented by bis-phosphines particularly those having less than 40 carbon atoms per molecule.

Examples of suitable symmetrical triaryl phosphines are triphenyl phosphine, tritolyl phosphine, trichlorophenyl phosphine, tri-trifluoromethylphenyl phosphine, trifuryl phosphine, trithienyl phosphine, tri-cyanophenyl phosphine, tri-difluorophenyl phosphine.

Examples of suitable unsymmetrical phosphines are phenyl bis-ethoxy-phenyl phosphine, phenyl bis-butylphenyl phosphine, diphenyl phenoxphenyl phosphine, diphenyl octylphenyl phosphine, diphenyl chlorophenyl phosphine, diphenyl nitrophenyl phosphine, diphenyl methylsulfonylphenyl phosphine, diphenyl benzothienyl phosphine, diphenyl biphenyl phosphine, diphenyl terphenyl phosphine, diphenyl pyrryl phosphine.

Examples of suitable bis-phosphines and polyphosphines are bis-diphenyl-phosphino benzene, bis-diphenylphosphino naphthalene, bis-diphenylphosphino diphenyl oxide, bis-diphenyl biphenyl, bis-diphenyl-phosphino diphenylmethane, tris-diphenylphosphino napthalene.

The triaryl phosphine ligands and the rhodium carbonyl hydride ligand complexes of the present invention are prepared via methods taught in the literature. Volume 1, pages 32 to 77 and 124 to 224 of a monograph on "Organic Phosphorus Compounds," edited by G. M. Kosolapoff and L. Maier, published by J. Wiley & Sons, Ltd., New York, 1972, is a reference on ligand synthesis and properties. The present tris-(triaryl phosphine) rhodium carbonyl hydride complexes, particularly the triphenyl phosphine complex, were disclosed in a monograph entitled, "Transition Metal Hydrides" edited by E. L. Mutterties, published by Marcel Dekker, Inc., New York, N.Y., 1971. In the present process, the catalytic complexes are most advantageously prepared from their readily available precursors in situ. Exemplary precursors are acetylacetonato dicarbonyl rhodium and hexarhodium hexadecarbonyl.

The absolute concentration of the triaryl phosphine ligand in the reaction mixture must be high in the present process. The phosphine is a major component of the reaction mixture. The phosphine concentration ranges from 1 to 3.5 phosphorus equivalent per liter, preferably from about 1 to 2.7 equivalent per liter. In the case of triphenyl phosphine this means a weight concentration in the solvent alone ranging from about 32.9 to 95%. A further preferred concentration range is 1.5 to 2.7 phosphine equivalent per liter, i.e., 49 to 88%.

The stabilization of the present catalyst system is directly proportional to the phosphine equivalency of the ligand. On a molar basis non-chelating bis-phosphine are twice as effective stabilizers. As previously discussed, the concentration of the excess triarylphosphine ligand is also directly related to the n/i ratio of aldehyde products.

OXYGENATED SOLVENTS

The present process employs simple oxygenated solvent components selected from the group consisting of monoalcohols, simple alkyl esters of carboxylic acids, branched aldehydes and acetals. These oxygenated solvents were not anticipated by the known prior art. Monoalcohols and alkyl esters of carboxylic acids, such as n-butanol and ethyl benzoate, did not provide homogeneous liquid mixtures throughout the full course of the related Union Carbide hydroformylation process as disclosed in columns 11 and 12. Table I of U.S. Pat. No. 4,148,830 by Pruett and Smith, Branched aldehydes and acetals were not suggested to our knowledge as solvent components for triarylphosphine rhodium complex catalyst systems.

The monoalcohol solvent components of the present hydroformylation process are preferably by-products of the process. In 1-butene hydroformylation the preferred solvents include n-amyl alcohol and 2-propylheptanol. These are both derived from the main n-valeraldehyde product via a combination of hydrogenation and aldolization reactions:

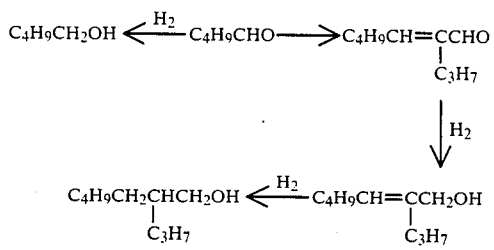

The preferred carboxylic acid esters are derived from carboxylic acid derivatives of hydroformylation products; e.g.

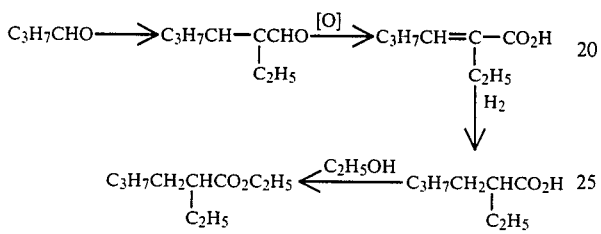

The branched aldehyde solvent components are minor hydroformylation products. For example isovaleraldehyde, 2-propyl-2-heptenal and 2-propylheptanal are by-products of 1-butene hydroformylation

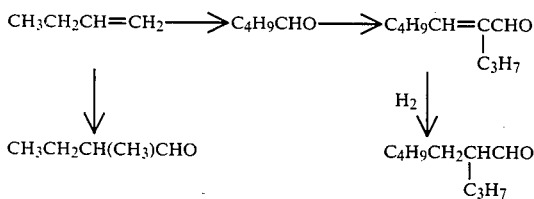

The acetal solvents are also derived from aldehyde products and alcohol by-products, e.g. in the case of 1-butene

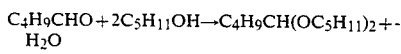

These oxygenated solvent components are by-products of the present continuous high temperature hydroformylation process while in the prior art continuous process oxygenated solvents were the trimers and tetramers derived from the aldol adduct of the aldehyde product, e.g.

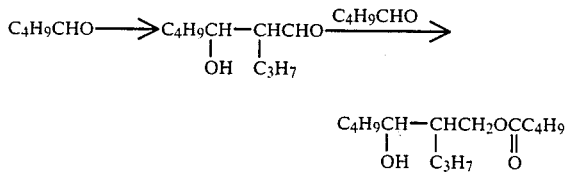

In the present process, the aldol adduct molecule rapidly loses a mole of water to form the unsaturated aldehyde which is expected to inhibit hydroformylation, e.g.

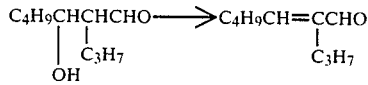

In the present process the unsaturated aldehyde is not an effective inhibitor and is largely hydrogenated to provide the corresponding saturated aldehyde and alcohol which are desirable solvent components.

In the 90° to 120° C. temperature region of the prior art, the rate of formation of the main trimer solvent components increases with increasing temperature. In contrast, the present high temperature process produces different, generally lower boiling, oxygenated solvent compounds at a much reduced rate. This is advantageous because an unnecessary excess of oxygenated compounds reduces the useful reactor volume and too much nonvolatile formation hinders the maintenance of constant liquid volume due to more difficult product flash-off.

The present process operates at such temperatures that aldehyde product concentration and thus aldolization are kept at a minimum by a more effective flash-off. While in the prior art process, described in column 1, Table I of U.S. Pat. No. 4,247,486 by Brewster and Pruett, the aldehydes concentration in the reactor is 35%, in the present process it is less than 15%.

When the present process is operated, semi-continuously or with constant liquid takeoff, the aldehyde condensation products are removed in time to avoid having them as the main components of the reaction mixture.

The main reactive solvent of the present process is the triarylphosphine which is the major component of the reaction medium. As described this solvent ligand interacts with the catalytic complexes and thereby stabilizes them. Although the main function of the excess triaryl phosphine is that of a catalyst stabilizer, it also acts as a solvent. Its functioning as a solvent can be improved by appropriate substitution. For example, unsymmetrical mono- or dialkyl substituted triphenyl phosphines can be used instead of triphenyl phosphine itself.

To assure the solubility of the olefin reactants in the liquid reaction medium and thus carry out homogeneous hydroformylation, the olefin reactant has preferably 4 or more carbons. In the case of ethylene and propylene the preferred total pressure is preferably increased above 250 psi which is in contrast to the low pressure propylene hydroformylation disclosed in U.S. Pat. No. 4,108,905 by Wilkinson.

On the other hand the olefin is not a major solvent component in the continuous process and the dissolved olefin concentration is preferably between 1 and 10%. The concentration of total hydrocarbons is preferably less than 15%.

Olefinic Reactants

The preferred olefin reactants for the hydroformylation process of the present invention are ethylene and its mono and disubstituted derivatives. The substituents are preferably alkyl and substituted alkyl, more preferably alkyl. Mono-substituted derivatives, particularly α-olefins are preferred. The preferred carbon number is 2 to 40. Olefins having 4 to 12 carbon atoms are particularly preferred. The specifically preferred olefin reactant is 1-butene. Exemplary reactants are propylene, 2-methylpentene-1, butene-2, octene-1, pentene-1, allyl alcohol, allyl acetate, allyl t-butyl ether, acrolein dimethyl acetal, methyl oleate; 1,7-octadiene, dicyclopentadiene, trivinyl cyclohexane, 1,4-polybutadiene, acrylonitrile, methyl acrylate, acetal derivatives of acrolein, 2-butene, 4-octene.

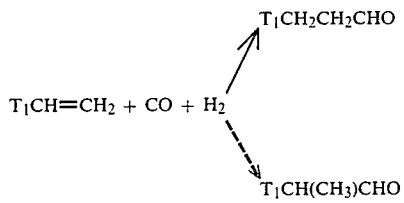

A high n/i ratio of products is also facilitated by reduced CO partial pressure. However, in contrast to the Union Carbide process sufficiently high n/i ratios can be achieved at CO partial pressures above 25 psia and with equimolar mixtures of $H_2$ and CO reactants.

The size, i.e., steric demand of the $T_1$ substitutent also affects the selectivity. In the case of propylene, having the small methyl group for $T_1$, the selectivity to the n-product is relatively small. 1-Butene, with ethyl for $T_1$, is hydroformylated with surprisingly higher selectivity. 3-Methyl-1-butene, where $T_1$ equals i-propyl reacts even much more selectively. Apparently, the bulkier and more branched $T_1$ groups hinder the attack on the internal, $\beta$-vinylic carbon.

The preferred monosubstituted olefins are $C_4$ to $C_{40}$ n-1-olefins, wherein $T_1$ is n-alkyl. The most preferred reactant is 1-butene. Ratios of n/i-products are preferably above 6, more preferably above 9.

As far as the terminal versus internal attack of unsymmetrically substituted olefins is concerned, the disubstituted compound is a highly specific but less reactive reagent in hydroformylation. It leads to mostly terminal, so called n-aldehydes:

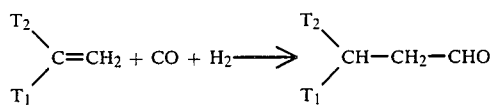

wherein the meaning of T is the same as described above. Specifically, preferred reagents of this type are isobutene, 2-methylbutene, 2-methylpentene, 2-ethylhexene, 2,4,4,-trimethylpentene.

It was found that in the case of these unsymmetrical olefins it is advantageous to use a nearly equimolar mixture of synthesis gas. Thus the preferred range of $H_2$/CO is from about 3/2 to $\frac{2}{3}$. CO partial pressures preferably above 25 psia, more preferably above 60 psia, are used.

The symmetrically disubstituted olefins such as linear internal olefins, slowly react at their internal vinylic carbons to provide the corresponding branched aldehydes, e.g.,

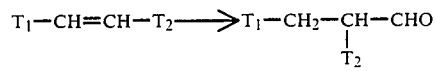

wherein the meaning of T is as previously stated. Preferred reagents of this type are butene-2 and pentene-2.

For a selective production of the above branched aldehydes, high CO partial pressures are preferred. Thus the preferred process conditions are those described for the unsymmetrically substituted olefins. However, these linear nonsubstituted internal olefins, can be also used for the production of straight chain aldehydes preferably via a combined isomerization, hydroformylation process. The course of such a process in the case of 2-butenes feed is indicated by the following scheme.

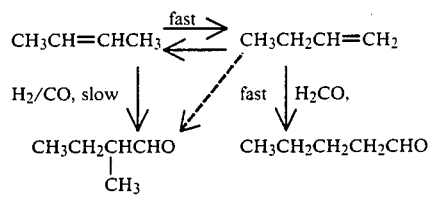

Fast olefin isomerization is essential for the success of this combined process. This is assured by keeping the CO isomerization inhibitor concentration at a minimum. To achieve high n/i product ratios, the triarylphosphine concentration should be above 2 $\overline{M}$ in this combined process.

The present hydroformylation process can be advantageously operated using a mixed olefinic feed. Using mixtures of three different types of preferred olefins, the most reactive 1-n-olefin component could be selectively converted to the corresponding n-aldehyde. For example, the 1-butene component of a mixture of isomeric butenes preferably of 1- and 2-butenes can be selectively hydroformylated to provide n-valeraldehyde. Similarly 1-pentene and 3-methyl-butene can be terminally hydroformylated using an isomeric mixture of pentenes such as those present in light catalytically cracked naphtha.

The isomerization rates of linear olefin reactants and/or the rates of branched aldehyde product isomer formation can be accelerated by using sterically crowded triarylphosphine ligands preferably those substituted in the ortho-position such as tri-o-tolyphosphine. Using these ligands, aldehyde products having comparable n/i ratios can be produced from 1-olefin feeds, such as propylene, and mixtures of isomeric linear olefins such as n-butenes.

The increased rates and reduced n/i product ratios of the above sterically crowded catalyst systems are due to steric decompression resulting in a higher rate of active specie formation and in a change of equilibria among the complex intermediates, in favor of the bis-triarylphosphine rhodium dicarbonyl hydride, e.g.

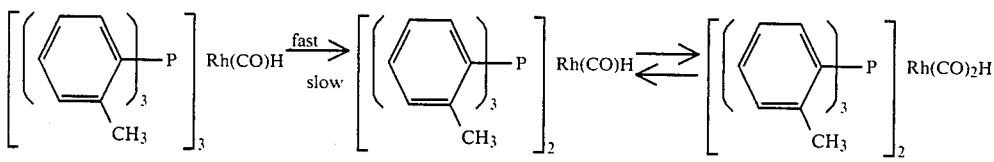

For the stabilization of these catalyst systems high phosphine ligand concentrations and increased CO partial pressures are required. The preferred CO partial pressure is in excess of 60 psi.

Synthesis Gas Reactants

The synthesis gas reactant mixture of $H_2$ and CO of the present process can be employed at varying pressures and in varying $H_2$ to CO ratios, preferably ranging from 0.67 to 15. For producing a high n/i ratio of aldehyde products it is more preferred to operate at $H_2/CO$ ratios between 2.5 to 15.

The present high temperature process operates under conditions wherein the hydroformylation rate is directly rather than inversely proportional to the CO partial pressure. Additionally, the selectivity to the n- plus i-aldehyde products i.e. total aldehyde selectivity is significantly increased at higher CO partial pressures. The increased CO partial pressure significantly reduces the rate of 1-olefin isomerization to the more stable, but less reactive internal olefins. Increased CO partial pressure is particularly important in the hydroformylation of $C_4$ and higher 1-n-olefins. Thus the present process is operated at remarkably high CO partial pressures. A preferred range of CO partial pressures is between 25 and 500 psia. A more preferred range is between 60 and 500 psia.

The partial pressure of hydrogen is usually not critical in the present process. The preferred $H_2$ range is between 25 and 500 psia.

Process Conditions

Besides influencing the catalyst structure the total pressure, it is important to maintain sufficient dissolved olefin concentration in the liquid phase, thereby providing a satisfactory reaction rate. An upper ceiling of the total pressure is established in the continuous product flash-off process where the difficulties of product removal in the vapor phase increase with added pressure. The range of total pressure in the present process is from about 100 to a 1500 psia, preferably from 150 to 700 psia, more preferably from 250 to 500 psia.

The present hydroformylations are carried out at temperatures between about 120° C. and 200° C., preferably between about 130° C. and 200° C. The high concentration of excess phosphine ligand and the high partial pressure of CO allow high temperature selective operation more preferably ranging from 140° to 200° C. even from 150° to 200° C. The selection of hydroformylation temperature depends on the molecular weight of the olefin feed and the preferred mode of operation. Higher temperatures are desired when higher olefins, such as $C_4$ and higher, are to be reacted to a high olefin conversion in a continuous product flash-off operation.

The present hydroformylation process is preferably carried out in the liquid state. The process can be operated batchwise, semicontinuously and continuously. In a typical batch operation, the reactor is charged with the triaryl phosphine, additional solvent and/or olefin and the rhodium catalyst complex or its precursor and brought to reaction conditions. The reactants, i.e., olefin, CO and $H_2$ are then introduced at the required pressure as the reaction proceeds. The $H_2/CO$ ratio is kept approximately constant during the reaction by appropriate $H_2/CO$ feed. In an exemplary semicontinuous operation, some of the reaction mixture is removed when a certain olefin conversion is reached. The products are then separated from this mixture, preferably in the vapor phase. The rest is returned to the hydroformylation reactor. In a continuous operation, products are continuously removed from the reactor in the liquid and/or in the gaseous state.

Continuous Mode of Operation

A continuous operation of the present process is preferred. One mode of the continuous operation removes the product in the gas phase. In another mode, the product is removed in the liquid phase and then separated from the ligand/catalyst and reactants, the latter being returned to the reactor. Distillation is the preferred method for product separation. As a rule, the triarylphosphine ligand is less volatile than the product and remains in the distillation residue with the catalyst complex and stabilizes the catalyst complex. The triaryl phosphine can contain minor amounts of other t-phosphines such as alkyl diaryl phosphines.

When the continuous product removal is in the gas phase, it is preferred to have a primary flash-off operation in which the product, condensation by-products, reactants and optionally some of the ligand and inert feed components are removed without fractionation. This mixture is then cooled with or without a pressure drop to provide a crude separation of the product as a liquid condensate and a gaseous mixture of $H_2/CO$ for recirculation. This condensate is then distilled, preferably at a reduced pressure to provide the pure product. A potential overhead fraction of the distillation is unconverted olefin which can be returned to the reactor either as a gas or as a liquid. A potential bottom fraction of the distillation is the triaryl phosphine ligand which can be recirculated to the reactor in the liquid phase.

In contrast to the prior art of Brewester et al. patent there is no recycle of the aldehyde product to maintain a certain reactor volume. The reactor volume is controlled by triarylphosphine ligand addition. Other factors determing the reactor volume are: the relative product formation and purge rates and the amount of the higher boiling by products.

It is particularly suprising that while the amount of "trimer" by-products is sharply reduced in the present process, small amounts of other aldehyde derivatives are formed which are advantageously used as the main nonreactive solvent components. As already discussed, the new solvent medium of the present process comprises monoalcohols, simple alkyl esters, acetals and branched aldehydes. These solvent compounds are less volatile than the primary products but more volatile than the trimers and tetramer of the prior art. Due to their slower rate of formation and increased volatility, they are particularly advantageous in a product flash-off operation.

As such, one aspect of the present invention defines an improved method for continuous hydroformylation with a catalyst system of improved stability and selectivity comprising reacting, dissolved $C_2$ to $C_{10}$ olefin i.e. feed with CO and $H_2$ in a homogeneous liquid phase medium at temperatures between 200° C. and at temperatures between about 120° and 200° C., and at a total pressure of 100 to 1000 psi to selectively produce n-aldehydes in the presence of a tris-triarylphosphine rhodium carbonyl hydride complex catalyst free from halogen on the rhodium wherein said reaction medium comprises a minimum of 1 mole per kg phosphorus equivalent of excess triaryl phosphine ligand as a catalyst stabilizer modifier and oxygenated solvents mainly comprising carboxylic acid esters of monohydric alcohols, free monohydric alcohols, acetals and branched aldehydes and wherein the reactants are continuously introduced into the liquid reaction mixture and at least some of the aldehyde products are continuously removed in the gas phase medium during the reaction. The improvement in the stability and selectivity is effected by an appropriate combination of high triarylphosphine concentration and increased CO partial pressure. Preferably, this process includes the recirculation of some unreacted feed and volatile by products, particularly synthesis gas and catalyst and ligand and wherein at least some of the aldehyde products are continuously removed, said improvement being effected by using an appropriately high $H_2/CO$ ratio in the range of about 2.5 to 10 and an appropriately high concentration of free triaryl phosphine as the major stabilizing component of the reaction mixture.

A unique advantage of the present process is that it can be operated at high temperatures without losing its selectivity and activity. The activity loss is typically less than 0.5% per day, preferably less than 0.3% per day. In a continuous product flash-off operation, increased temperature means that the vapors removed contain a higher percentage of products which allows higher conversions. While typical olefin conversions in prior art processes are below 30%, the present process allows olefin conversions in excess of 40% per pass. Operating in this preferred manner allows aldehyde production rates ranging from 0.5 to 5 g mole/liter per hour.

The present high temperature product flash-off process can also provide a better utilization of $H_2$ and CO. When smaller $H_2$ to CO ratios are used at high temperature, higher olefin conversions are obtained, a smaller volume of synthesis gas is recirculated.

The present continuous product flash-off method is carried out using known techniques described for butene-1 hydroformylation in our copending applications of Ser. Nos. 120,971 and 295,193 by A. A. Oswald, T. G. Jermansen, A. Westner and I. Huang, filed on Feb. 12, 1980 and on Aug. 21, 1981, respectively.

Specifically, the present invention provides an improved method for the continuous hydroformylation of butene-1 with a catalyst system of improved stability and selectivity comprising reacting a butene-1 feed with CO and $H_2$ in a homogeneous liquid phase medium at temperatures between about 120° and 160° C. and at a total pressure in the range of 100 to 700 psi to selectively produce n-valeraldehyde in the presence of tris-triphenylphosphine rhodium carbonyl hydride complex catalyst free from halogen on the rhodium wherein said reaction medium comprises a minimum of 2.2 mole per kg excess triphenylphosphine as a catalyst stabilizer modifier and oxygenated solvents comprising amyl alcohol, amyl propylheptanoate, valeraldehyde diamyl acetal and propylheptanal, wherein the reactants are continuously introduced into the liquid reaction mixture and wherein some of the aldehyde products are continuously removed in the gas phase and separated by condensation while the unreacted $H_2$ and CO reactants are recirculated, said process being carried out with long term maintenance of catalyst activity and selectivity in such a manner that the activity loss is below 0.5% per day. A particular mode of operating this process comprises the removal of at least a part of the free triphenyl phosphine ligand with some aldehyde in the gas phase wherein said ligand is preferably recirculated in the liquid phase.

EXAMPLES

In the following the practice of the present invention will be illustrated by Examples. At first, the preparation and properties of the triarylphosphine rhodium complex catalyst systems will be discussed. Thereafter, detailed batch hydroformylation studies using these systems will be disclosed to show the results of changing the catalyst composition and operational parameters. Finally, continuous hydroformylation studies will be discussed to demonstrate the formation and use of new oxygenated solvents and the stability of the present catalyst system.

Example 1

Preparation of Triphenylphosphine Rhodium Carbonyl Hydride Complex Catalysts

The triphenylphosphine and other triarylphosphine ligands of the present catalyst system must be essentially free from halogen, especially chlorine. Chloride impurities were usually removed e.g. by washing a toluene solution of the ligand with 10% aqueous sodium hydroxide solution. Triphenylphosphine, and other crystalline triarylphosphine ligands were preferably purified e.g. from phosphine oxides, by recrystallization from polar solvents such as $C_1$ to $C_4$ alcohols.

Chloride free tris-triphenylphosphine rhodium carbonyl hydride and other triarylphosphine complexes were preferably prepared starting with acetylacetonato rhodium dicarbonyl or tetrakis-triarylphosphine rhodium hydride; e.g.

$$CH_3COCHCOCH_3Rh^+(CO)_2 + 3\ Ph_3P + H_2 \longrightarrow$$

$$(Ph_3P)_3Rh(CO)H + CH_3COCH_2COCH_3 +$$

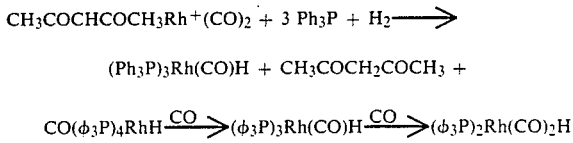

When starting with the dicarbonyl compound and excess triarylphosphine ligands both atmospheric and superatmospheric hydrogen readily provide the monocarbonyl hydride. The tetrakis-phosphine hydride leads to the monocarbonyl hydride if atmospheric CO is used for a short period. Under CO pressure the dicarbonyl hydride is formed.

Beside triphenylphosphine compounds, complexes of trifluorophenylphosphine, trimethoxyphenylphosphine, ortho and para-tritolylphosphine, bis-chlorophenylphenylphosphine, bis-diphenylphosphinobenzene, ortho-tolyl diphenylphosphine and ortho-methoxyphenyl diphenylphosphine were prepared.

For the isolation of the crystalline carbonyl hydrides, preferably ethanolic solutions of the starting reactants were used. The products were crystallized in the pure form as the reaction proceeded. The complexes were usually fairly soluble in toluene. Two percent toluene solutions were readily prepared at room temperature in the absence of oxygen. Excess triarylphosphine ligand had a stabilizing effect.

Example 2

Nuclear Magnetic Resonance Spectroscopic Properties of Triphenylphosphine Rhodium Carbonyl Hydride Complexes The NMR characteristics of the rhodium carbonyl hydride complexes of triphenylphosphine and other triarylphosphine ligands were determined to allow their structural characterization in solution and to predict their catalytic behavior.

In general, these studies started with an about 3% solution in a 90/10 mixture of toluene and deuterotoluene of the monocarbonyl hydride complex. The solutions were placed into pressure NMR tubes equipped with Teflon valves. Varying excess of triarylphosphine ligand and varying pressure of $H_2/CO$ were used. The mixtures were equilibrated by shaking prior to study. NMR parameters were usually determined at $-30°$ C. using $^{31}P$ NMR experiments with a JEOL FX 900 multinuclear NMR spectrometer. When required the experimental conditions were adjusted, i.e. the $^1H$-$^{31}P$ decoupling was removed to eliminate nuclear Overhauser enhancement and longer delays between pulses were employed to provide sufficient time for spin lattice relaxation in order to determine the relative populations of free and rhodium bound alkyl diphenyl phosphine and TPP. Chemical shifts were measured by assigning a shift of 0 PPM to the frequency at which 1M $H_3PO_4$ would resonate.

The tris-triphenylphosphine rhodium monocarbonyl hydride has a $^{31}P$ chemical shift, of $\delta_{Ph_3P}$ 38.7 ppm and a coupling constant, $J_{P\text{-}Rh}$, of 153 cps. The parameters of the bis-triphenylphosphine rhodium dicarbonyl hydride are: $\delta$34.8 ppm; $J_{P\text{-}Rh}$, 137 cps.

EXAMPLES (1–81)

General Method of Batch Hydroformylation

The hydroformylation of 1-butene to provide linear pentanal and branched 2-methyl-butanal products was selected as the main reaction for the study of the present process. The main triaryl phosphine catalyst ligand employed was triphenyl phosphine.

In the batch hydroformylation experiments, a 300 ml Hastelloy autoclave was used. The autoclave was equipped with baffles and a highly effective, impeller type stirrer. During the experimental runs, the stirrer was operated at 1500 rpm. The $H_2/CO$ reactant was introduced into the liquid reaction mixture at the bottom, close to the stirrer through a sintered inductor to assure small bubble size and instantaneous mixing.

As catalyst precursors, pure, halide free rhodium dicarbonyl acetylacetonate, RhAcac(CO)$_2$, from Engelhard Industries, and triphenylphosphine, from Aldrich Chemical Co., Inc., were used. These precursors reacted readily and, in the presence of hydrogen, were converted to the desired tris-phosphine rhodium complex. Comparative runs, using these precursors, gave results identical to those obtained in experiments starting with the pure tris-phosphine rhodium complex, from Engelhard Industries, plus triphenyl phosphine.

According to the standard procedure, appropriate amounts of the free Ph$_3$P were employed to make up 80 g of mixture with 2-ethylhexyl acetate as a solvent. This solvent exhibited the solvent characteristics of carboxylic acid alkyl esters in general. The Ph$_3$P and RhAcac(CO)$_2$ compounds were placed into the autoclave at first and were then followed by the solvent. The amount of rhodium was selected to achieve a conversion of 50% of the olefin reactant in 5 to 40 minutes. Most often the amount of the rhodium complex used provided $5 \times 10^{-4}$ mole/liter, 0.5 mM, rhodium concentration after the addition of the olefin reactant in the starting reaction mixture. This corresponds to about 54 ppm Rh, or 54 mg Rh per kg.

When less than 15 g triphenyl phosphine was used, the autoclave could be closed after the addition of the ligand. With higher ligand quantities, the prior heating of the autoclave under $N_2$ to produce a liquid mixture was necessary.

The charged autoclave was closed, flushed by nitrogen and heated to the reaction temperature. Thereafter, 20 g of the olefin reactant, usually 1-butene, were pressured into the autoclave above the liquid level by the initial synthesis gas mixture, usually 5/1 $H_2/CO$. In general, the initial gas was added until a total pressure of 2500 kPa was reached. The autoclave was then connected to the approximately 1 to 1 $H_2/CO$ run gas provided at the same pressure. Up to this point, the autoclave was not stirred to avoid reaction.

On starting the stirrer, the hydroformylation proceeded without any induction period. Synthesis gas feed was provided at the bottom of the reactor, through a pressure regulating valve. This valve was set to maintain the starting pressure, usually 2500 kPa. The exact $H_2/CO$ ratio of the feed gas was varied from 50/50 to 56/44 to maintain the initial $H_2/CO$ ratio in the autoclave. In general, $H_2/CO$ ratios above one were required to maintain the initial $H_2/CO$ ratios. This was, in part, due to the hydrogenation side reaction of the olefin. The other factor was the decreasing 1-butene partial pressure during the reaction. Higher $H_2/CO$ feed ratios were needed at the higher reaction temperatures, apparently due to the increased relative rate of olefin hydrogenation and increased butene partial pressure. Thus the present hydroformylations were run at approximately constant $H_2/CO$ rate, i.e. constant pCO, in a manner distinct above all the known batch processes of the prior art.

The progress of the hydroformylation was followed on the basis of the amount of 1:1 $CO/H_2$ consumed. The latter was calculated on the basis of the pressure drop in a 1 liter $CO/H_2$ cylinder. Reactant conversion, calculated on the basis of CO consumption, was plotted against the reaction time to determine the reaction rate. The reaction rate was expressed as the fraction of the theoretical $CO/H_2$ requirement consumed per minute (k min$^{-1}$). The reactions were run to 50% olefin conversion calculated on the basis of $H_2/CO$ consumed. Up to that conversion level there was no change of the reaction rate or any other sign of catalyst instability.

When the reaction was to be discontinued, the $CO/H_2$ feed valve was shut and the autoclave was immediately cooled with a water-ice bath. When the reaction mixture was at about 15° C., the synthesis gas was released slowly. Working in this manner, no significant loss of the 1-butene reactant occurred.

An analysis of the final $H_2/CO$ mixture in the reactor was carried out using a 75 ml gas sample taken from the head space of the hot reactor, at the end of the reaction, immediately after the stirrer was stopped and the feed valve was closed. The final $H_2/CO$ ratio was thus determined using a Carle 111H gas chromatograph.

The cold residual liquid was analyzed after opening the autoclave. The overall analysis of the liquids was carried out using a Hewlett Packard 5840 gas chromatograph. An SP 2100 column and a flame ionization detector were used. The more volatile hydrocarbon components were determined as a group. The individual higher boiling aldehydes and other compounds were separated. Due to the lower response of this detector to aldehydes, the intensity of the hydrocarbon peaks was multiplied by a factor of 0.7 to obtain the relative weight percentages of hydrocarbon by products versus aldehydes. The n- and i-aldehyde isomers were usually well separated to allow a quantitative determination of the n/i ratios.

The individual volatile hydrocarbons were separated by the Carle 111H chromatograph system. The first column of this system retained the higher boiling components of the liquid sample. The hydrocarbon components of the exiting gases were separated on another column and determined by a thermal conductivity detector.

The results of the 1-butene hydroformylation studies will be presented and discussed mainly to show three factors in rhodium hydroformylation. These factors are the concentration of the excess $Ph_3P$ ligand, the temperature of the reaction mixture and the partial pressure of CO reactant. These factors were studied in detail because their complex relationship determines the alternate mechanisms of rhodium hydroformylation and provides guidance in setting the optimum parameters for the present process.

In accord with the literature, the reaction rate showed a simple first order relationship in the olefin reactant and the rhodium catalyst concentration. Neither the olefin nor the rhodium concentration affected the selectivity of the reaction. The observed rates showed an excellent rate correlation with the rhodium concentration. Therefore, rates normalized for 1M rhodium concentration could be used to compare catalyst activities.

Examples 3–12

Effect of Increased Excess Triphenylphosphine Concentration on 1-Butene Hydroformylation at Various Temperatures Triphenyl phosphine rhodium complex catalyst systems were studied in 2-ethylhexyl acetate solvent. The triphenylphosphine concentration was $0.14\overline{M}$ and $0.56\overline{M}$, i.e. 4.7 and 18.5 wt. by wt%, in the solvent. The previously described standard batch hydroformylation procedure was used with a 5/1 $H_2/CO$ reactant ratio under 350 psia (about 2500 kPa) pressure at temperatures ranging from 115° to 160° C. The rhodium concentration was varied from 0.1 to 0.25 m$\overline{M}$ to achieve 50% olefin conversion between 8 and 28 minutes reaction time. The work was aimed at determining the effect of the $Ph_3P$ concentration at different temperatures. The data obtained are shown by Table I.

The results show that the fourfold increase in phosphine concentration had a large adverse effect on the rate of hydroformylation but also a definite-positive effect on the n/i ratio of the aldehyde products (Experiments of Example Nos. 3–7 versus 8–12).

As the temperature of the reaction was increased from 115° to 145°, the rate inhibiting effect of the increased phosphine concentration was decreased. The ratio of normalized reaction rates [calculated for 1M rhodium concentration] was 3.2 at 115° C. for the 0.14 versus 0.56M ligand system (Example No. 3 vs. 8). The same systems showed a reaction rate ratio of 2.2 at 145° C. (Example No. 6 vs. 11).

It is also noted that these examples clearly show that at these high ligand concentrations the n/i ratio of aldehyde products is mainly determined by the concentration of the triphenylphosphine ligand, [P], rather than by the P ligand to Rh complex ratio. The experiments of Examples 9 to 11 which had a higher concentration but lower P/Rh ratio provided a much higher n/i ratio than Examples 4 to 7. This finding is in contrast with the prior disclosures of the patent and scientific literature, which discloses that the ligand to rhodium ratio, P/Rh, rather than ligand concentration, [P], determines the selectivity. The results of the present examples clearly show that this is not the case under the conditions of the present process.

TABLE I

EFFECT OF TRIPHENYLPHOSPHINE CONCENTRATION ON RHODIUM HYDROFORMYLATION AT VARIOUS TEMPERATURES

Reactions at 2500 kPa (24.7 Atm), with 5/1 Initial $H_2/CO$, and 20 g 1-Butene plus 80 g Mixture of Triphenylphosphine Plus 2-Ethylhexyl Acetate. Using $AcacRh(CO)_2$ as Catalyst Precursor

| Example No. | Catalyst System Parameters | | | | $H_2/CO$ Ratio Feed | $H_2/CO$ Ratio Final | $H_2/CO$ Consumption Dependent Factors (50% Conversion) | | Reaction Time Min. | Aldehyde Linearity | | Selectivities, Mol % | | | | |
|---|---|---|---|---|---|---|---|---|---|---|---|---|---|---|---|---|
| | | | | | | | Rate Constant k, min$^{-1}$ | | | | | Aldehydes | | | By-Products | |
| | $Ph_3P$ Conc. M | React. Temp. °C. | Rh Conc. $10^3 \times$ M | P/R Ratio | | | Observed | At 1 M [Rh] | | n/i Ratio | $\frac{100\,n}{n+i}$ % | Total | n- | i- | 2-Butenes | Butane |
| 3 | 0.14 | 115 | 0.25 | 564 | 52/48 | 5.0 | 0.074 | 300 | 9 | 4.7 | 82.5 | 93.0 | 76.7 | 16.3 | 5.2 | 1.8 |
| 4 | | 125 | 0.05 | 2822 | 52/48 | 4.6 | 0.025 | 500 | 28 | 4.3 | 81.0 | 93.7 | 75.9 | 17.8 | 5.0 | 1.3 |
| 5 | | 135 | 0.05 | 2822 | 53/47 | 5.1 | 0.033 | 660 | 21 | 4.2 | 80.9 | 89.4 | 72.3 | 17.1 | 8.2 | 2.4 |
| 6 | | 145 | 0.05 | 2822 | 54/46 | 5.8 | 0.040 | 800 | 18 | 4.0 | 80.2 | 83.0 | 66.6 | 16.4 | 13.4 | 3.6 |
| 7 | | 160 | 0.05 | 2822 | 56/44 | 6.7 | 0.040 | 800 | 20 | 3.7 | 78.8 | 70.5 | 55.6 | 14.9 | 24.3 | 5.2 |
| 8 | 0.56 | 115 | 0.50 | 1121 | 52/48 | 5.2 | 0.046 | 92 | 15 | 9.4 | 90.4 | 91.3 | 82.5 | 8.8 | 6.8 | 1.9 |
| 9 | | 125 | 0.25 | 2240 | 52/48 | 5.1 | 0.045 | 180 | 16 | 8.9 | 89.9 | 90.6 | 81.4 | 9.1 | 6.8 | 2.6 |
| 10 | | 115 | 0.25 | 2240 | 53/47 | 5.2 | 0.069 | 276 | 10 | 8.2 | 89.1 | 87.4 | 77.9 | 9.5 | 8.8 | 3.6 |
| 11 | | 145 | 0.25 | 2240 | 54/46 | 5.1 | 0.089 | 356 | 8 | 7.3 | 88.0 | 85.4 | 75.2 | 10.2 | 10.7 | 3.9 |

TABLE I-continued
EFFECT OF TRIPHENYLPHOSPHINE CONCENTRATION ON RHODIUM HYDROFORMYLATION AT VARIOUS TEMPERATURES
Reactions at 2500 kPa (24.7 Atm), with 5/1 Initial $H_2/CO$, and 20 g 1-Butene plus 80 g Mixture of Triphenylphosphine Plus 2-Ethylhexyl Acetate, Using $AcacRh(CO)_2$ as Catalyst Precursor

| Example No. | $Ph_3P$ Conc. M | Catalyst System Parameters | | | | | $H_2/CO$ Consumption Dependent Factors (50% Conversion) | | Reaction Time Min. | n/i Ratio | Aldehyde Linearity $\frac{100n}{n+i}$ % | Selectivities, Mol % | | | | |
|---|---|---|---|---|---|---|---|---|---|---|---|---|---|---|---|---|
| | | React. Temp. °C. | Rh Conc. $10^3 \times$ M | P/R Ratio | $H_2/CO$ Ratio Feed | $H_2/CO$ Ratio Final | Rate Constant k, min$^{-1}$ Observed | At 1 M [Rh] | | | | Aldehydes | | | By-Products | |
| | | | | | | | | | | | | Total | n- | i- | 2-Butenes | Butane |
| 12 | | 160 | 0.10 | 560 | 56/44 | 5.2 | 0.031 | 310 | 26 | 6.1 | 85.9 | 69.0 | 59.3 | 9.7 | 22.9 | 8.1 |

Of course, the reaction rate was also affected by the temperature. However, Arrhenius plots of the data indicated that above 125° C., the apparent activation energy of the reaction was decreasing at all $Ph_3P$ concentrations. While an activation energy of about 25 kcal/mole was calculated on the basis of the rate increase from 110° to 125° C., the apparent $E_a$ would be 5 kcal/mole or less on the basis of the 145° and 160° C. data. The large drop in the apparent value of the "activation energy" is an indication of the change in the chemistry of hydroformylation. Therefore, temperature effects in the 110° to 125° C. range, are different from those in the 145°-160° C. range.

As the temperature was increased, the positive effect of increased phosphine concentration on the n/i ratio was maintained. However, the n/i ratios were dropping with increasing reaction temperatures at both phosphine concentrations. Nevertheless, a higher n/i ratio (6.1) was obtained at 160° at 0.56M $Ph_3P$ (Example No. 12), than at 115° at 0.14M $Ph_3P$ concentration (4.7, Example No. 3). The adverse effect of increased temperatures on the n/i ratio can be apparently overcome by appropriately high concentrations of the excess phosphine ligand.

The selectivity of the reaction for the total (n+i) aldehydes produced was also adversely affected by increased reaction temperatures. However, the total aldehyde percentage was not affected significantly by the concentration of the phosphine ligand. In both series of experiments, the total aldehydes decreased with increasing temperatures because increasing amounts of cis- and trans-2-butenes isomerization and butane hydrogenation products were formed.

Examples 13-25
Effect of Increased CO Partial Pressure at $1\overline{M}$ Triphenylphosphine Concentration on 1-Butene Hydroformylation The effect of increased CO partial pressure on hydroformylation in the presence of the triphenylphosphine rhodium complex catalyst system was studied at a further increased triphenylphosphine concentration. In these experiments, the excess ligand concentration in the ester solvent was $1\overline{M}$, i.e. 32.9 wt%. The conditions used were similar to those of the previous examples. However, different CO partial pressures were obtained by carrying out the experiments at several total pressure levels: 1250 kpa (~175 psia); 2500 kpa (~350 psia) and 5000 kPa (~700 psia). The pCO was approximately doubled by doubling the pressure of the 5 to 1 $H_2/CO$ gas. The effect of increased pressure was studied at temperatures ranging from 90° to 160° C. Of course, the partial pressure of the 1-butene reactant increased with the temperature. At 160° C. it was about 600 kPa as indicated by a control experiment. The experimental data are shown in Table II.

A comparison of the experimental data obtained at 2500 kPa (Examples 14, 16, 18, 20, 22, and 14) with the data obtained in Examples 3 to 12 shows that at the highest ligand concentration the use of high reaction temperature has several unexpected advantages: The adverse effect of high ligand concentration on the rate is minimized while the beneficial effect on the n/i ratios is mostly maintained. Thus a normalized rate constant of 256 and an n/i ratio of 7.6 were obtained even at 160° C.

The results of Table II shows that the increased pressure of CO affected the reaction rate, the n/i ratio and the total percentage of aldehydes. The rate was increased and the n/i ratio was decreased dependent on the reaction temperature. The percentage of the total aldehydes was increased by the increased CO partial pressure at all reaction temperatures.

TABLE II
EFFECT OF CO PARTIAL PRESSURE ON RHODIUM HYDROFORMYLATION AT $1\overline{M}$ TRIPHENYLPHOSPHINE CONCENTRATION AT VARIOUS TEMPERATURES
Reactions at 2500 and 5000 kPa (24.7 and 29.5 Atm) with 5/1 Initial $H_2/CO$ and 20 g 1-Butene Plus 80 g Mixture of 20.4 g Triphenylphosphine Plus 2-Ethylhexyl Acetate, Using $AcacRh(CO)_2$ as Catalyst Precurser

| Example No. | Reaction Conditions | | | Reaction System Rh Conc. $10^3 \times$ M | $H_2/CO$ Ratio Feed | $H_2/CO$ Ratio Final | $H_2/CO$ Consumption Dependent Factors (50% Conversion) Rate Constant k, min$^{-1}$ | | Reaction Time Min. | n/i Ratio | Aldehyde Linearity $\left[\frac{100n}{n+i}\right]$ % | Selectivities, Mole % | | | | |
|---|---|---|---|---|---|---|---|---|---|---|---|---|---|---|---|---|
| | Temp. °C. | Pressure, kPa Total | pCO | | | | Observed | At 1 M Rh | | | | Aldehydes | | | By-Products | |
| | | | | | | | | | | | | Total | n- | i- | 2-Butenes | Butane |
| 13 | 90 | 1250 | 208 | 3.0 | 51/49 | 4.4 | 0.031 | 10 | 23 | 25.4 | 96.2 | 86.8 | 83.5 | 2.3 | 10.4 | 2.8 |
| 14 | | 2500 | 417 | 3.0 | 52/40 | 5.0 | 0.033 | 11 | 22 | 12.3 | 92.5 | 89.6 | 82.8 | 6.8 | 7.7 | 2.7 |
| 15 | | 5000 | 833 | 3.0 | 52/48 | 4.0 | 0.031 | 10 | 22 | 7.0 | 87.5 | 91.1 | 79.7 | 11.4 | 5.8 | 3.1 |
| 16 | 110 | 2500 | 417 | 0.5 | 52/48 | 5.1 | 0.017 | 34 | 40 | 12.9 | 92.8 | 91.3 | 84.8 | 6.5 | 5.7 | 3.0 |

TABLE II-continued

EFFECT OF CO PARTIAL PRESSURE ON RHODIUM HYDROFORMYLATION AT .1 $\overline{M}$ TRIPHENYLPHOSPHINE CONCENTRATION AT VARIOUS TEMPERATURES Reactions at 2500 and 5000 kPa (24.7 and 29.5 Atm) with 5/1 Initial $H_2$/CO and 20 g 1-Butene Plus 80 g Mixture of 20.4 g Triphenylphosphine Plus 2-Ethylhexyl Acetate, Using AcacRh(CO)$_2$ as Catalyst Precurser

| Example No. | Reaction Conditions Temp. °C. | Pressure, kPa Total | pCO | Reaction System Rh Conc. $10^3 \times$ M | $H_2$/CO Ratio Feed | $H_2$/CO Ratio Final | $H_2$/CO Consumption Dependent Factors (50% Conversion) Rate Constant k, min$^{-1}$ Observed | At 1 M Rh | Reaction Time Min. | n/i Ratio | Aldehyde Linearity $\left[\dfrac{100\,n}{n+i}\right]$ % | Selectivities, Mole % Aldehydes Total | n- | i- | By-Products 2-Butenes | Butane |
|---|---|---|---|---|---|---|---|---|---|---|---|---|---|---|---|---|
| 17 |  | 5000 | 833 | 0.5 | 52/48 | 5.7 | 0.022 | 44 | 31 | 7.8 | 88.7 | 90.8 | 80.5 | 10.3 | 6.8 | 2.4 |
| 18 | 125 | 2500 | 417 | 0.5 | 52/48 | 4.7 | 0.050 | 116 | 12 | 11.9 | 92.3 | 89.1 | 82.2 | 6.9 | 7.9 | 3.1 |
| 19 |  | 5000 | 833 | 0.5 | 52/48 | 4.9 | 0.061 | 124 | 11 | 7.6 | 88.4 | 90.4 | 79.9 | 10.5 | 6.9 | 2.7 |
| 20 | 135 | 2500 | 417 | 0.5 | 54/46 | 6.4 | 0.070 | 156 | 9 | 12.0 | 92.7 | 84.2 | 78.1 | 6.1 | 10.7 | 5.1 |
| 21 |  | 5000 | 833 | 0.5 | 54/46 | 5.8 | 0.007 | 174 | 8 | 8.5 | 89.4 | 87.8 | 78.6 | 9.3 | 8.3 | 3.9 |
| 22 | 145 | 2500 | 417 | 0.25 | 54/46 | 5.7 | 0.050 | 200 | 14 | 11.2 | 91.8 | 81.2 | 74.6 | 6.6 | 13.3 | 5.5 |
| 23 |  | 5000 | 833 | 0.25 | 54/46 | 5.6 | 0.072 | 288 | 9 | 8.1 | 89.0 | 86.7 | 77.2 | 9.5 | 9.2 | 4.1 |
| 24 | 160 | 2500 | 417 | 0.25 | 56/44 | 5.6 | 0.064 | 256 | 11 | 7.6 | 88.4 | 78.9 | 69.7 | 9.2 | 15.8 | 5.3 |
| 25 |  | 5000 | 833 | 0.25 | 56/44 | 6.1 | 0.100 | 400 | 6 | 7.6 | 88.3 | 82.8 | 73.0 | 9.7 | 11.3 | 6.0 |

The effect of pCO on the hydroformylation rate was negligible at the low reaction temperature of 90° C. At this temperature, no significant rate decrease was observed even at the further reduced pCO of about 208 kPa (Example Nos. 13-15). As the reaction temperature was increased from 110° to 160° C., increasing pressures had increasing effects on the rate. In the 110° to 135° C. range, the reaction rate at the doubled pressure was about 1.1 times greater (Examples 16-21). At 145° C., the rate at the doubled pressure was about 1.4 times greater. At 160° C., the increased rate was almost 1.6 times the value at the lower pressure.

The adverse effect of the increased pCO on the n/i ratio, on the other hand, decreased with increasing reaction temperatures. Doubling the pCO from 417 to 833 kPa at 90° C. reduced the n/i ratio from 12.3 to 7. The same pressure increase at 160° C. did not produce a significant change; the n/i ratios were 7.6 and 7.5, respectively.

The doubling of the CO partial pressure had about the same positive effect on the total amounts of aldehydes produced at all reaction temperatures. The increase in the percentage of n+i aldehydes was from 2.5 to 5.9% without any clear temperature correlation. At the lower temperature range of 90°-135° C., this increase was the result of the much increased i-aldehyde production. The selectivity to the n-aldehyde isomer was decreased with the increased pCO in this lower temperature range. In the higher temperature range, the selectivity to both the n- and the i-aldehydes increased with the increased pressure. At 145° and 160° C., the total aldehyde increase was 5.5 and 5.9%, respectively. Most of this increase was due to the reduced isomerization to 2-butenes.

Examples 26-33

Effect of CO and $H_2$ Partial Pressure at 2M Triphenylphosphine Concentrations on 1-Butene Hydroformylation at 145° and 160° C.

The effect of pressure changes on hydroformylation in the presence of the tris-triphenylphosphine rhodium carbonyl hydride based catalyst system was further studied at 2.2$\overline{M}$, 72%; triphenylphosphine concentration in the ester solvent. The data obtained are shown in Table III. The first part of the table, i.e., Example Nos. 26-29, shows an extension of determining the effect of double 5/1 $H_2$/CO pressure. These experiments were carried out at 145° or 160° C. The second part, Example Nos. 28, 30, 33, shows the effect of changing $H_2$/CO ratios at a total pressure of 2500 kPa (350 psia) and a reaction temperature of 145° C.

The results of Table III shows that, at 2.2$\overline{M}$ Ph$_3$P concentration, high CO partial pressures and low $H_2$/CO ratios can be used and high n/i aldehyde product ratios can still be maintained.

The first four experiments (Example Nos. 26-29) show that the doubling of the pressure of the 5 to 1 $H_2$/CO gas produces more rate increase at the 2.2$\overline{M}$ Ph$_3$P concentration than it did at 1$\overline{M}$ Ph$_3$P. For comparison, see Example Nos. 22 to 25 of Table II. At 2.2$\overline{M}$ Ph$_3$P and 160° C. reaction temperature, the reaction rate was about 2.4 times higher at the increased pressure. The effect of the increased pressure on the n/i ratio was qualitatively the same as in the corresponding experiments of Table II at lower Ph$_3$P concentration. However, at the increased Ph$_3$P concentration, the lowest n/i ratio observed with the 5 to 1 $H_2$/CO reaction was higher, i.e., 14.6 instead of 7.5. Finally, it is noted that the effect of increased pressure on the n+i aldehyde selectivity was virtually the same in these experiments as was previously found at 1$\overline{M}$ Ph$_3$P concentration (for comparison see Table II, Example Nos. 22 to 25).

TABLE III

EFFECT OF CO AND $H_2$ PARTIAL PRESSURE ON HIGH TEMPERATURE RHODIUM HYDROFORMYLATION AT 2.2 $\overline{M}$ TRIPHENYLPHOSPHINE CONCENTRATION

Reactions at 2500 and 6000 kPa (24.7 and 29.6 Atm) with Varying Initial Ratios of $H_2/CO$ and 20 g 1-Butene Plus 80 g Mixture of 56.8 g Triphenylphosphine and 2-Ethylhexyl Acetate, Using Acac $Rh(CO)_2$ as Catalyst Precursor

| Example No. | Reaction Conditions Temp. °C | Pressure, kPa pCO | pH₂ | Rh Conc. 10³ × M | Reaction System H₂/CO Ratio Feed | H₂/CO Ratio Initial | H₂/CO Ratio Final | $H_2/CO$ Consumption Dependent Factors (50% Conversion) Rate Constant k, min⁻¹ Observed | At 1 M Rh | Reaction Time Min. | n/i Ratio | Aldehyde Linearity $\left[\dfrac{100\,n}{n+i}\right]$ % | Selectivities, Mole % Aldehydes Total | n- | i- | By-Products 2-Butenes | Butane |
|---|---|---|---|---|---|---|---|---|---|---|---|---|---|---|---|---|---|
| 26 | 160 | 417 | 2083 | 0.25 | 56/44 | 5 | 6.2 | 0.027 | 108 | 28 | 14.2 | 93.4 | 78.6 | 73.5 | 5.2 | 16.2 | 5.2 |
| 27 |  | 834 | 4166 | 0.25 | 56/44 | 5 | 6.7 | 0.064 | 256 | 11 | 14.7 | 93.6 | 82.9 | 77.6 | 5.3 | 11.3 | 5.8 |
| 28 | 145 | 417 | 2082 | 0.25 | 54/46 | 5 | 5.9 | 0.023 | 92 | 32 | 21.7 | 95.6 | 80.0 | 76.5 | 3.5 | 14.3 | 5.7 |
| 29 |  | 834 | 4166 | 0.25 | 54/46 | 5 | 5.5 | 0.042 | 168 | 17 | 14.6 | 93.6 | 85.3 | 79.8 | 5.5 | 10.0 | 4.7 |
| 30 | 145 | 625 | 1875 | 0.25 | 54/46 | 3 | 4.0 | 0.029 | 116 | 25 | 19.4 | 95.1 | 82.1 | 78.1 | 4.0 | 13.4 | 4.4 |
| 31 |  | 1000 | 1500 | 0.25 | 54/46 | 1.5 | 2.2 | 0.032 | 128 | 23 | 14.0 | 93.7 | 84.8 | 79.4 | 5.4 | 11.9 | 3.3 |
| 32 |  | 1250 | 1250 | 0.25 | 54/46 | 1 | 1.6 | 0.032 | 128 | 24 | 13.3 | 93.0 | 88.2 | 82.1 | 6.1 | 9.1 | 2.7 |
| 33 |  | 2250 | 250 | 0.25 | 50/50 | 0.1 | 0.37 | 0.027 | 108 | 33 | 6.7 | 87.5 | 88.6 | 77.5 | 11.1 | 9.8 | 1.6 |

The second group of experiments of Table III (Example Nos. 30–33) shows that, at constant pressure, the ratio of $H_2/CO$ has a complex effect on the rate. In contrast, a consistent decrease of n/i ratio and increase of the percentage of n+i aldehydes is observed when the $H_2/CO$ ratio is dropped from 5 to 0.1.

The normalized reaction rate is substantially increased, from 92 to 128, as the $H_2/CO$ ratio is decreased from 5 to 1.5 (Example Nos. 28, 30, and 31). This decrease of $H_2/CO$ ratio corresponds to an increase of CO partial pressure from 417 to 1000 kPa as it is shown by the table. In this pressure region the rate sustantially increased with the increased pCO.

As the $H_2/CO$ ratio is further decreased from 1.5 to 1 and then 0.1, very little change of the reaction rate occurs (Example Nos. 31 to 33). The change from 1 to 0.1 $H_2/CO$ ratio is accompanied by a rate decrease rather than increase. This means that in the pCO range of 1000 to 2250 kPa there is very little rate dependence. Indications were that at a 1 to 1 ratio of $H_2/CO$ or greater, the rate dependence on the partial pressure of hydrogen was insignificant.

Examples 34–38

Effect of 2.5–3M Triphenylphosphine Concentration on 1-Butene Hydroformylation at 145° C.

In a series of examples, 1-butene was hydroformylated using the above described technique in the presence of tris-triphenylphosphine rhodium carbonyl hydride and extremely high concentrations of excess triphenylphosphine in the ester solvent: 2.5M (82%); 2.7M (88.4%); 2.9M (95%). One experiment was carried out in the absence of any ester solvent (3.0M $Ph_3P$, 100%). All the reactions were carried at 145° C. under about 2500 kPa pressure using a 5 to 1 $H_2/CO$ ratio. The results are shown in Table IV.

The data show a continued positive effect of the increasing phosphine ligand concentration on the n/i ratio of the aldehyde products. In the 2.2–2.9$\overline{M}$ $Ph_3P$ range the total aldehyde selectivity was also maintained although the n+i values were artificially high due to hydrocarbon loss on opening the autoclave reaction vessel (Example Nos. 34 to 36). However, when the triphenylphosphine and the 1-butene reactants were employed without the ester solvent a highly apparent increase of the hydrocarbon by-products was observed. Consequently, the total aldehyde selectivity was low.

Examples 39–43

Effect of Triphenylphosphine Concentration and CO Partial Pressure on the Hydroformylation Iosmerization of 2-Butene and/or 1-Butene

In another series of examples, 2-butene was used as a hydroformylation feed at 145° C. in the presence of the triphenylphosphine rhodium catalyst system. A high excess of triphenylphosphine in the ester solvent was used to demonstrate combined isomerization hydroformylation to yield the n-aldehyde product (Examples 39 to 40). Increased CO partial pressures were used to inhibit isomerization of the 2-butene and to increase hydroformylation selectivity to the i-aldehyde. The results are shown in Table V.

TABLE IV

HYDROFORMYLATION OF 1-BUTENE WITH TRIS-TRIPHENYL PHOSPHINE RHODUIM CARBONYL HYDRIDE IN THE PRESENCE OF INCREASING PHOSPHINE LIGAND CONCENTRATION

Reaction at 145° C., 350 psi (24.7 Atm) of 5/1 $H_2/CO$ (64/46 Feed) and 20 g 1-Butene Plus 80 g Mixture of Phosphine Plus 2-Ethylhexyl Acetate, Using $AcacRh(CO)_2$ as Catalyst Precursor

| Identification Example Number | Catalyst System Parameters Ligand Conc. [I] [H] in Mix. at Start | % Wt. in Solvent | Rh Conc. mM | l./Rh | $H_2/CO$ Consumption Dependent Factors (50% Conversion) $H_2/CO$ Ratio Final | Rate Constant kl min⁻¹ | Reaction Time min. | n/i Ratio | Product Linearity $\dfrac{n \times 100}{n+i}$ % | Hydroformylation Selectivity Total n+i % | n- % | i- % | By-Product Selectivity, % 2-Butenes | Butane |
|---|---|---|---|---|---|---|---|---|---|---|---|---|---|---|
| 34 | 2.5 | 82 | 5 | 5000 | 4.0 | 0.06 | 11 | 20.7 | 95.4 | 88.5 | 84.4 | 4.1 | 9.1 | 2.4 |
| 35 | 2.7 | 88.4 | 5 | 5400 | 4.5 | 0.04 | 17 | 23.7 | 96.0 | 92.3 | 88.5 | 3.8 | 6.0 | 1.7 |
| 36 | 2.9 | 95 | 5 | 5600 | 3.4 | 0.05 | 13 | 22.0 | 95.6 | 93.1 | 89.0 | 4.1 | 5.1 | 1.9 |
| 37 | 3.0 | 100 | 20 | 1500 | 5.6 | 0.09 | 9.5 | 31.0 | 96.9 | 73.3 | 71.0 | 2.3 | 19.6 | 7.1 |
| 38 | 3.0 | 100 | 5 | 6000 | 5.0 | 0.03 | 25 | 25.4 | 96.2 | 78.6 | 75.6 | 3.0 | 15.9 | 5.4 |

The data shows that under 2500 kPa (350 psia) pressure and with an $H_2/CO$ ratio of 10, the use of triphenylphosphine as a solvent provided the highest n/i ratio of the series (4.2, Example 39). However, this system was extremely prone to CO starvation when using batch hydroformylation techniques. This resulted in operational difficulties and increased butane by-product formation.

At the $2.2\overline{M}$ (72%) triphenylphosphine concentration n/i aldehyde product ratios ranging from 3.3 to 0.28 were produced at increasing CO partial pressures (Example Nos. 40 to 43). As the CO partial pressure increased from about 250 kPa (~35 psia) to about 2500 kPa (350 psia), isomerization and hydrogenation became increasingly inhibited. Instead of 1-butene hydroformylation, more and more 2-Butene hydroformylation took place. The normalized reaction rates increased with pCO but still remained relatively low. Large rhodium concentrations had to be used to reach the desired rates. This results in some pentanol by-product formation.

Examples 44–54

Effect of Process Parameters on Propylene Hydroformylation in the Presence of the Triphenylphosphine Rhodium Complex Catalyst System The effect of the main hydroformylation process parameters, $Ph_3P$ concentration, reaction temperature and pressure was also investigated with propylene feed using a 5/1 mixture of $H_2/CO$. The results are shown in Table VI.

TABLE V

HYDROFORMYLATION OF 2-BUTENE WITH THE $Ph_3P$—Rh CATALYST SYSTEM AT DIFFERENT $H_2/CO$ RATIOS
20 g 2-Butene 80 g Mixture of 2-Ethyhexyl Acetate Plus $Ph_3P$ and Acac $Rh(CO)_2$ Catalyst Precursor

| Example No. | Reaction Conditions °C. | Reaction Conditions kPa | Ligand Conc. M | $H_2/CO$ Ratio | Rate Constant $K_N$ at 1 M Rh | n + i Ratio | Selectivity, Mole % Aldehydes n + i | Selectivity, Mole % Aldehydes n | Selectivity, Mole % Aldehydes i | Pentanol | 2-Butenes | Butane |
|---|---|---|---|---|---|---|---|---|---|---|---|---|
| 39 | 145 | 2500 | 3.0 | 10 | 1.2 | 4.2 | 80.2 | 63.8 | 16.4 | 4.5 | 0.6 | 14.7 |
| 40 | 145 | 2500 | 2.2 | 10 | 1.9 | 3.3 | 85.6 | 65.7 | 20.0 | 1.3 | 1.1 | 12.0 |
| 41 | 145 | 2500 | 2.2 | 5 | 2.0 | 2.5 | 87.7 | 52.9 | 24.8 | 1.3 | 1.4 | 9.6 |
| 42 | 145 | 2500 | 2.2 | 1 | 2.3 | 0.81 | 95.9 | 43.0 | 52.9 | 1.4 | 0.7 | 1.9 |
| 43 | 145 | 5000 | 2.2 | 1 | 3.8 | 0.28 | 97.2 | 21.4 | 75.7 | 1.3 | 0.4 | 1.1 |

TABLE VI

EFFECT OF TRIPHENYLPHOSPHINE CONCENTRATION, TEMPERATURE AND CO PARTIAL PRESSURE ON PROPYLENE HYDROFORMYLATION WITH RHODIUM COMPLEX CATALYST SYSTEMS
Reactions at 2500 and 5000 kPa (24.7 and 29.5 Atm) with 5/1 Initial $H_2/CO$ and 20 g Propylene Plus 80 g Mixture of Triphenylphosphine Plus 2-Ethylhexyl Acetate Using $AcacRh(CO)_2$ as a Catalyst Precursor

| Example No. | Reaction Conditions $Ph_3P$ Conc M | Reaction Conditions React. Temp. °C. | Reaction Conditions Pressure kPa | Reaction System Rh Conc $10^3 \times$ M | Reaction System $H_2/CO$ Ratio Feed | $H_2/CO$ Consumption Dependent Factors (50% Conversion) $H_2/CO$ Ratio Final | Rate Constant k, min$^{-1}$ Observed | Rate Constant At 1 M Rh | Reaction Time Min. | Aldehyde Linearity n/i Ratio | Aldehyde Linearity $\frac{100n}{n+i}$ % | Selectivities, Mole % Aldehydes Total | Selectivities, Mole % Aldehydes n- | Selectivities, Mole % Aldehydes i- | Propane |
|---|---|---|---|---|---|---|---|---|---|---|---|---|---|---|---|
| 44 | 0.14 | 125 | 2500 | 0.10 | 55/45 | 5.3 | 0.025$^a$ | 250 | 30 | 3.3 | 76.6 | 98.9 | 75.7 | 23.2 | 1.1 |
| 45 | 0.56 | 125 | 2500 | 0.50 | 55/45 | 4.6 | 0.048$^a$ | 96 | 16 | 7.3 | 86.0 | 96.5 | 86.7 | 11.8 | 1.5 |
| 46 | 1.0 | 110 | 2500 | 2.00 | 55/45 | 5.4 | 0.051 | 26 | 14 | 11.3 | 91.9 | 98.8 | 90.8 | 8.0 | 1.2 |
| 47 | 1.0 | 125 | 2500 | 1.00 | 54/46 | 4.3 | 0.061$^a$ | 61 | 16 | 11.1 | 91.7 | 98.0 | 89.9 | 8.1 | 2.0 |
| 48 | 1.0 | 135 | 2500 | 0.25 | 55/45 | 4.7 | 0.019$^a$ | 76 | 48 | 8.6 | 89.5 | 98.6 | 88.3 | 10.3 | 1.4 |
| 49 | 1.0 | 145 | 2500 | 0.50 | 56/44 | 5.0 | 0.054$^a$ | 108 | 17 | 7.4 | 88.1 | 97.5 | 85.9 | 11.6 | 2.5 |
| 50 | 1.0 | 110 | 5000 | 1.00 | 55/45 | 5.7 | 0.022 | 22 | 32 | 5.7 | 85.1 | 99.2 | 84.5 | 14.7 | 0.8 |
| 51 | 1.0 | 125 | 5000 | 0.50 | 55/45 | 5.7 | 0.028 | 56 | 25 | 6.2 | 86.1 | 98.7 | 85.0 | 13.7 | 1.3 |
| 52 | 1.0 | 145 | 5000 | 0.25 | 55/45 | 4.9 | 0.045 | 180 | 16 | 5.5 | 84.5 | 98.8 | 83.4 | 15.3 | 1.2 |
| 53 | 2.2 | 125 | 2500 | 1.00 | 55/45 | 4.1 | 0.026$^a$ | 26 | 67 | 16.3 | 94.2 | 96.2 | 90.7 | 5.5 | 3.8 |
| 54 | 2.2 | 145 | 5000 | 0.50 | 55/45 | 4.8 | 0.054 | 108 | 13 | 8.8 | 89.8 | 97.6 | 87.6 | 10.0 | 2.4 |

$^a$The rate increased with the conversion. The observed value is at the higher rate.

In general, the data show that surprisingly lower n/i ratios of the aldehyde products are obtained with propylene than with 1-butene. However, the effects of process parameters are qualitatively similar.

In the case of propylene, the high triphenylphosphine concentrations of the present high temperature process are particularly required to provide the desired high n/i ratios butyraldehydes. The effect of temperature on rate acceleration is pronounced without any significant adverse effect on selectivity. Finally, the effect of doubled pressure which increases the pCO from about 1250 kPa (175 psia) to about 2500 kPa (350 psia), also results in definite rate acceleration. The adverse effect of increased pCO on the n/i ratio is minimized at the maximum $Ph_3P$ concentration (Example 54).

Examples 55–62

Effect of Olefin Structure on Hydroformylation at 145° C. in the Presence of 1M Triphenylphosphine To further show the effect of the olefin reactant structure on the activity and selectivity of the present triphenylphosphine rhodium complex catalyst in an ester solvent system, olefins of varying carbon number and structural type were studied. The reactions were carried out with the usual batch hydroformylation technique using 5 to 1 $H_2/CO$ at 145° C. under 2500 kpa (350 psia) pressure. The results are shown in Table VII.

The results show that the bulky tris-phosphine complex catalyzed hydroformylation is highly dependent of the steric crowding of the olefin reactant. Both the reaction rate and the selectivity are affected. Substitution of the vinylic carbons has a drastic inhibitory effect. However, α- and β-olefins leads to very high selectivities for hydroformylation at the terminal carbon.

As far as the $C_3$ to $C_6$ 1-n olefins were concerned, the catalyst was highly effective (Example No. 55). However, propylene gave a lower n/i ratio of aldehyde products than the rest under analogous test conditions (Example Nos. 55 vs. 56–58). The high n/i product ratio of the $C_4$ to $C_6$ olefins is due to the increased steric crowding of the internal vinylic carbon. It is interesting to observe that the isomerization of 1-hexene was limited to the formation of 2-hexene.

The results of propylene hydroformylation also illustrated that the $H_2/CO$ reactant ratio is particularly difficult to control in the present batch hydroformylation tests when highly volatile olefins are used. The increased loss of the more volatile olefins to the gas phase also affects the apparent rate of hydroformylation. Therefore, the present results are qualitative in character.

isomer was formed. The hydroformylation of 2-ethyl-1-hexene showed a similarly high selectivity. No olefin isomerization was detected.

Examples 63 and 64

Effect of CO Partial Pressure on the Hydroformylation of 1-Octene at 155° C. in the Presence of 2.2M triphenylphosphine 1-Octene was hydroformylated in two experiments at 350 psi in the manner described in the previous examples. The starting solvent catalyst mixture contained 59% (2.2M) of triphenyl phosphine and 5 mM acetylacetonato dicarbonyl rhodium. The 1-octene reactant (20 g) was pressured into the mixture by $CO/H_2$ at the reaction temperature, i.e., at 155° C.

In Example 63, a 5/1 $H_2/CO$ ratio of initial feed was used while a 1/1 $H_2/CO$ feed was employed in Example 64. In both cases, a run gas of 54/46 $H_2/CO$ was used. The final $H_2/CO$ ratios after 50% conversion were 5.5 and 1.1, respectively.

At the 5/1 $H_2/CO$ reactant ratio, the hydroformylation occurred at a rate only half of that obtained with 1/1 $H_2/CO$, i.e., k min$^{-1}$ of 0.12 versus 0.24. However, the 5/1 $H_2/CO$ resulted in a much higher n/i ratio; i.e.,

TABLE VII

EFFECT OF OLEFIN STRUCTURE ON RHODIUM HYDROFORMYLATION AT 1 M TRIPHENYLPHOSPHINE CONCENTRATION AT 145° C.
Reactions at 2500 kPa (24.7 Atm) with 5/1 Initial $H_2/CO$ and 20 g Olefin Plus 80 g Mixture of 20.4 g Triphenylphosphine Plus 2-Ethylhexyl Acetate, Using AcacRh(CO)$_2$ as Catalyst Precursor

| | | Reaction System | | $H_2/CO$ Consumption Dependent Factors (50% Conversion) | | | | Aldehyde Linearity | | Selectivities, Mole % | | | | |
|---|---|---|---|---|---|---|---|---|---|---|---|---|---|---|
| | | Rh | | | Rate Constant | | Reaction | | | | Aldehydes | | | By-Products | |
| Example No. | Olefin Reactant | Conc. $10^3 \times$ M | $H_2/CO$ Ratio Feed | $H_2/CO$ Ratio Final | k, min$^{-1}$ Observed | At 1 M [Rh] | Time Min. | n/i Ratio | $\frac{100n}{n+i}$ % | Total | n- | i- | 2-(1-) Olefin | Paraffin |
| 55 | $CH_3CH=CH_2$ | 1 | 60/40 | 16.2 | 0.055 | 55 | 13 | 13.0 | 90.7 | 96.4 | 87.4 | 9.0 | — | 3.6 |
| | | 1 | 56/44 | 4.1 | 0.091 | 91 | 7 | 7.4 | 88.1 | 90.2 | 86.5 | 11.3 | — | 1.8 |
| | | 1 | 54/46 | 2.0 | 0.101 | 101 | 7 | 6.0 | 85.8 | 90.4 | 84.5 | 13.9 | — | 1.6 |
| 56 | $CH_3CH_2CH=CH_2$ | 0.25 | 54/46 | 5.7 | 0.050 | 200 | 14 | 11.2 | 91.8 | 87.2 | 74.6 | 6.6 | 13.3 | 5.5 |
| 57 | $CH_3(CH_2)_2CH=CH_2$ | 0.25 | 51/49 | 4.6 | 0.065 | 260 | 11 | 10.6 | 91.4 | 87.2 | 79.7 | 7.6 | 8.3 | 4.5 |
| 58 | $CH_3(CH_2)_3CH=CH_2$ | 0.25 | 52/48 | 5.0 | 0.104 | 416 | 7 | 11.3 | 91.8 | 89.6 | 82.2 | 7.3 | 6.1 | 4.5 |
| 59 | $CH_3CHCH_2CH=CH_2$ <br> \| <br> $CH_3$ | 0.5 | 51/49 | 4.5 | 0.120 | 240 | 5 | 19.6 | 90.5 | 79.3 | 71.8 | 7.5 | 10.9 | 9.8 |
| 60 | $CH_3CH_2CHCH=CH_2$ <br> \| <br> $CH_3$ | 0.5 | 51/49 | 4.7 | 0.142 | 204 | 5 | 22.4 | 95.5 | 92.7 | 88.5 | 4.2 | 2.6 | 4.7 |
| 61 | $CH_3CH_2C=CH_2$ <br> \| <br> $CH_3$ | 5.0 | 54/46 | 5.0 | 0.030 | 6 | 22 | — | 100.0 | 90.7 | 90.7 | N11 | 2.5 | 5.7 |
| 62 | $CH_3CH=CHCH_3$ | 5.0 | 54/46 | 4.0 | 0.020 | 5.6 | 24 | 0.7 | 41.9 | 95.8 | 39.9 | 55.9 | (0.6) | 3.8 |

A comparison of 4- and 3-methyl-1-pentenes showed an interesting selective steric effect on the n/i ratio (Example Nos. 59 and 60). The 4-methyl substitution had no effect. The n/i ratio of the products of this isomer, 11, was about the same as that of 1-pentene and 1-hexene (Example Nos. 59 vs. 57, 58). The 3-methyl isomer was hydroformylated much more selectively at its terminal carbon. A high n/i ratio of 22.6 was obtained (Example No. 58), apparently due to selective steric inhibition. The rate of terminal hydroformylation was not adversely affected.

The hydroformylation rate of 2-methyl-1-butene showed a tremendous steric inhibition (Example No. 61). It was about 2.6% of the rate of 1-pentene hydroformylation. All the aldehyde formed was derived by terminal hydroformylation. Relatively little 2-olefin 21.6 versus 7.1. Both reaction mixtures appeared to remain stable. The extent of 1-octene isomerization to 2-octene was 10.2 and 5.1, respectively. No detectable amounts of the other isomers could be detected by capillary gas chromatography.

Examples 65 and 68

Effect of Conversion on the Hydroformylation of Isomeric Butenes

Two isomeric mixtures, one consisting of 1- and 2-butenes, the other composed of 1-, 2- and iso butenes, were hydroformylated to determine the effect of conversion on the selective hydroformylation of the most reactive component, 1-butene.

With both mixtures, the triphenylphosphine rhodium complex catalyst system was used at 0.1 mM Rh concentration in 2-ethylhexyl acetate solvent employing the already described experimental techniques. The concentration of excess triphenylphosphine was $1\overline{M}$. The reactions were carried out at 145° C. under 2500 kPa (350 psia) total pressure. A 5/1 mixture of $H_2/CO$ was used initially to reach this pressure and then a 54/46 or 53/47 feed gas was used to maintain it during the reaction.

In Example 65 a mixture of 1- and 2-butenes was hydroformylated to a 25% conversion of the total butenes. The normalized rate constant at 1M Rh was 110, an expected value on the basis of the concentration of the 1-butene component. The starting mixture of the olefin reactants and the remaining dissolved hydrocarbons in the final reaction mixture were analysed for isomer distribution. The percentages of isomeric butenes were the following:

| Composition of | 1-butene | cis-2-butene | trans-2-butene |
|---|---|---|---|
| Reactants | 46.3 | 21.2 | 30.3 |
| Unreacted Reactants | 27.7 | 30.3 | 44.0 |

The results indicate that the 1-butene component was selectively hydroformylated. This is supported by the high n/i ratio, 8.13, of the valeraldehydes produced. The n-butane selectivity was 5.9%.

In Example 66, an approximately equimolar mixture of 1-, 2- and i-butenes was similarly hydroformylated. However, in this case the reaction was carried out to 25% conversion of all the butenes, i.e. only slightly less than the approximate percentage of the 1-butene in the reactant mixture.

In contrast to the previous example, the rate of the reaction was not maintained throughout the experiment, but dropped to about half of the initial rate. The concentration of the highly reactive 1-butene became too low. The 2-butenes and some of the i-butene also reacted but at a low rate. The comparative percentages of the isomers of the reactant and unreacted butenes were the following:

| Composition of | 1-butene | 2-butenes | i-butene |
|---|---|---|---|
| Initial Reactant | 29.3 | 52.3 | 33.4 |
| Unreacted Reactants | 5.7 | 53.8 | 40.5 |

The n/i ratio of the aldehyde products was only 3.9. The selectivity to butanes, mostly n-butane, was 2.9%.

Examples 67 and 68

Hydroformylation of Allyl t-Butyl Ether

The hydroformylation of allyl t-butyl ether, a 3-alkoxy substituted 1-n-olefin, was also investigated in the present process with the previously described batch techniques in 2-ethylhexyl acetate solvent.

The triphenylphosphine rhodium complex catalyst system was used at a rhodium concentration of 0.25 mM (25 ppm) and 0.05 mM (5 ppm), respectively. The triphenylphosphine concentration was $1\overline{M}$ (32.9% in the solvent) in both experiments. The reactions were carried out at 145° C. at total pressures of 2500 kPa (350 psia) and 1250 kPa (175 psia), respectively.

In Example 67, the reaction was run at a 5/1 $H_2/CO$ reactant ratio using a feed gas ratio of 53/47. At the 0.25 $m\overline{M}$ Rh concentration, 50% conversion was reached in 90 seconds. On this basis, the normalized rate constant of this reaction is 2500, an extremely high value.

In spite of the potential CO starvation the expected hydroformylation reaction occurred selectively:

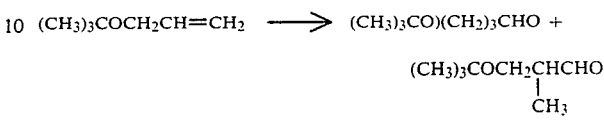

They were formed at a total selectivity of 19.4%. Hydrogenation selectivity to propyl t-butyl ether was very small, 3.5%.

In Example 68, lower rhodium concentration (0.025 mM) and lower pressure (1250 kPa) were used with 1/1 $H_2/CO$ ratio and 51/49 feed. The reaction was nevertheless very fast. It took 10 minutes to reach 50% conversion. The normalized rate was about 1480. Analyses of the reaction mixture indicated generally improved selectivity percentages: n+i, 92.2; n/i, 5.9; isomerization, 7.5; hydrogenation, 0.3.

Thus the results indicate a highly unusual but generally advantageous behavior for oxygen substituted olefins in the present process. The decreased ratio of $H_2/CO$ reactant and/or increased pCO have no adverse effect on the n/i ratio but a highly beneficial effect on the selectivity.

A comparison of the prior art "low temperature, little triphenylphosphine" allyl t-butyl ether hydroformylation process disclosed in European Patent Application No. 18,161 by N. Harris, A. J. Dennis and G. E. Harrison with the present work shows that high aldehyde selectivities were unexpectedly reached in the present process. The aldehyde selectivity at 100° C. was only 61.4% in the Harris et al. patent.

Examples 69–77

1-Butene Hydroformylation in the Presence of Rhodium Complexes of Substituted Triphenylphosphine Liquids 1-Butene was also selectively hydroformylated in the present high temperature process using catalyst systems based on rhodium complexes of substituted triphenylphosphine liquids as follows: trifluorophenylphosphine, trimethoxyphenylphosphine ortho- and para-tritolylphosphine, bis- chlorophenyl-phenylphosphine, bis-diphenylphosphino-benzene, orthotolyl diphenylphosphine, ortho-methoxy diphenylphosphine.

Examples 78–83

1-Butene Hydroformylation with the triphenylphosphine Rhodium Complex Catalyst System in the Presence and in the Absence of Propyldiphenylphosphine To determine the effect of mixed catalyst complex species containing two triarylphosphine and one alkyldiarylphosphine ligands per rhodium, the effect of adding minor amounts of n-propyldiphenyphosphine to the tris-triphenylphosphine rhodium complex based catalyst system was studied.

Comparative experiments were carried out, using 1-butene hydroformylation at 145° C. as a model reaction. The details of the reaction conditions and the data are shown by Table VIII. The results indicate that at low alkyldiarylphosphine concentration, e.g. in Example 79, there is no noticeable adverse effect on the reaction rate and n/i-aldehyde ratio but there is a significant desired effect, i.e. an increase of the selectivity to total aldehydes and a concurrent decrease in hydrocarbon by-product formation.

dium complex catalyst system was employed. A constant liquid level of the reaction mixture was maintained by an automatic return of the necessary amounts of the aldehyde product condensate.

The process parameters of the continuous runs at 100° and 140° C. were widely different by design at it is shown by Table IX. At the higher temperature, higher pressure plus increased ligand and rhodium concentration were required to achieve the desired selective reaction at a sufficient rate. On the other hand, less excess 1-butene and synthesis gas were needed at the higher temperature because less stripping gas was required for removing the valeraldehyde product in the vapor phase.

TABLE VIII

1-BUTENE HYDROFORMYLATION WITH TRIS-PHOSPHINE RHODIUM COMPLEX SYSTEMS HAVING VARYING RATIOS OF TPP AND ALKYL DIPHENYL PHOSPHINE LIGANDS

Reactions with 350 psi (24.7 Atm) of 5/1 $H_2/CO$, 20 g 1-Butene, 1 M Total Phosphine in 2-Ethylhexyl Acetate, introducing 54/46 $H_2/CO$ Feed Gas into Reaction Mixture, with $AcacRh(CO)_2$ Catalyst Precursor

| $Ph_2PR$ Ligand Structure | Example No. | Catalyst System Parameters | | | $H_2/CO$ Consumption Dependent Factors (50% Conversion) | | | Aldehyde Product Parameters | | | | By-Product Selectivity | |
|---|---|---|---|---|---|---|---|---|---|---|---|---|---|
| | | Temp. °C. | Phosphine Comp. Mole, % | | Rhodium Conc, mM | Ratio $H_2/CO$ Final | Constant k, $min^{-1}$ | Reaction Time (min) | Linearity | | Hydroformylation Selectivity | | | |
| | | | $Ph_3P$ | $Ph_2PH$ | | | | | n/i Ratio | n × 100 / n + i, % | Total n i, % | n- % | i- % | 2-Butenes | Butane |
| $Ph_2PC_3H_7$ | 78 | 145 | 100 | 0 | 0.5 | 5.3 | .104 | 7 | 10.7 | 91.5 | 80.4 | 73.6 | 6.9 | 13.2 | 6.4 |
| | 79 | 145 | 95 | 5 | 0.5 | 5.2 | .108 | 6.5 | 10.7 | 91.5 | 84.7 | 77.4 | 7.2 | 11.0 | 4.3 |
| | 80 | 145 | 90 | 10 | 0.5 | 5.1 | .100 | 7 | 10.4 | 91.4 | 86.2 | 78.8 | 7.4 | 9.4 | 4.5 |
| | 81 | 145 | 00 | 20 | 0.5 | 5.9 | .090 | 7.5 | 10.9 | 91.6 | 82.0 | 75.1 | 6.9 | 11.9 | 6.1 |
| | 82 | 145 | 50 | 50 | 0.6 | 6.4 | .071 | 10 | 10.9 | 91.6 | 86.2 | 79.0 | 7.2 | 9.1 | 4.6 |
| | 83 | 145 | 0 | 100 | 0.5 | 6.3 | .059 | 14 | 9.4 | 90.4 | 89.8 | 81.2 | 8.6 | 6.5 | 3.7 |

This unexpected effect at high triarylphosphine concentration and elevated temperature is one of the features of the present invention. At higher alkyldiarylphosphine concentrations, e.g. in Example 82, bis- and tris-(alkyldiarylphosphine)rhodium complexes are the main catalyst species. Hydroformylation with these latter catalysts of lower activity but further increased stability is the subject of our earlier referred, copending application Ser. No. 120,971.

Examples 84–88

Continuous Hydroformylation

Figure 1:
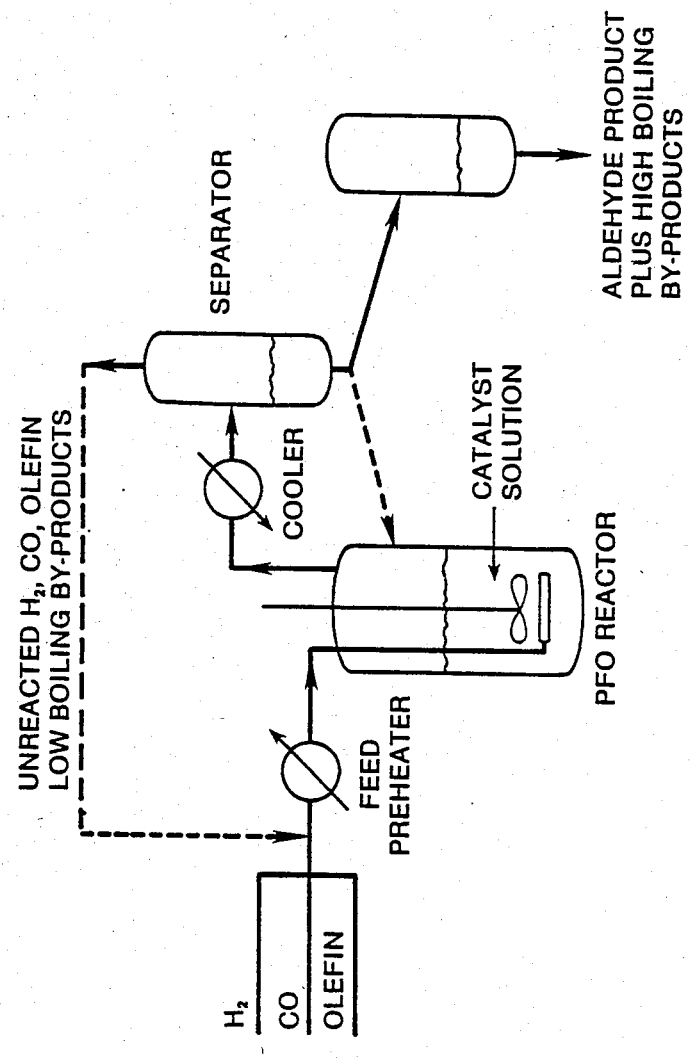
FIG. 1 shows an outline of the continuous hydroformylation unit of the present process with continuous product flashoff from the reactor (PFO).

The continuous high temperature hydroformylation process of the present invention was studied using butenes as reactants and product flash-off from the reactor (FIG. 1). The use of 1-butene was particularly preferred since it allowed a study of the concurrent isomerization reactions producing internal olefins, i.e. 2-butenes, as well. In view of this additional side reaction and the reduced volatility of the aldehyde products, selective 1-butene hydroformylation represented an added challenge over the usual prior art hydroformylation of propylene. To allow comparisons, triphenylphosphine rhodium complex based catalyst systems were used in all the continuous experiments.

Examples 84–85

The Effect of Temperature on Product Flash-Off in Continuous 1-Butene Hydroformylation To demonstrate the highly beneficial effects of increased reaction temperatures in continuous PFO hydroformylation, comparative experiments were carried out using 1-butene feed at 100° and 140° C. In both of these experiments "n-valeraldehyde trimers" were used as solvent components. A one liter solution of the rho- The results of the two runs show the expected qualitative differences in conversion and selectivity. At 140° C., the 1-butene conversion was 82%, i.e., more than three times that of the 100° C. conversion. This increase in conversion is only partially due to the lower 1-butene feed rate (2.8 vs. 4 m/hr/l). At the higher temperature 2.3 times more valeraldehyde is produced. The 140° C. product has a higher n/i ratio than the 100° C. product (29 vs 21). This occurred in spite of the reduced $H_2/CO$ ratio i.e., increased CO partial pressure.

The selectivity to by-products was generally greater at 140° C. The selectivities to butane and 2-butenes both just about doubled. There was surprisingly no increase in aldehyde dimer and trimer formation. The total selectivity is about 0.5%. However, there was an additional by-product about 2.8% amyl alcohol, at 140° C. The major problem was the poor activity maintenance. An activity loss of 5% per day was observed. In six days, this resulted in reducing the per pass 1-butene conversion from 83.1 to 65.5%.

Example 86

Continuous 1-Butene Hydroformylation With Activity Maintenance at 140° C.

To better stabilize the PFO hydroformylation catalyst system at 140° C., the excess triphenylphosphine concentration was further increased. The added trimer solvent and aldehyde recycle were eliminated. This resulted not only in a stable PFO operation but in a different catalyst system containing unexpectedly advantageous oxygenated compounds.

For the startup, the two liter reactor was charged with a warm, 930 ml toluene solution of about 524 g (2 moles) of triphenylphosphine and 2.34 g (10 molimoles) of rhodium dicarbonyl acetylacetonate. The reaction was run at 140° C. under a total pressure of 1275 kPa (185 psia). The reactants were introduced at the following feed rates in moles per hour: 1-butene, 2.95; $H_2$, 21.2 and CO, 7.18. The large excess of synthesis gas feed acted as a plentiful purge gas to minimize the aldehyde concentration.

In the first two days of operation, the toluene component of the reaction mixture was flashed off together with most of the valeraldehydes formed in the catalyst system. Some of the valeraldehydes remained as reactive solvent components.

TABLE IX

EFFECT OF TEMPERATURE ON CONTINUOUS HYDROFORMYLATION OF 1-BUTENE IN THE PRODUCT FLASH-OFF MODE WITH $Ph_3P$-Rh COMPLEX CATALYST SYSTEMS

|  | Example 84 100° C. Run | Example 85 140° C. Run |
|---|---|---|
| Pressure, kPa | 800 | 1275 |
| $PH_2$, kPa | 565 | 724 |
| $P_{CO}$, kPa | 69 | 138 |
| Rhodium Conc., mM | 2.50 | 4.44 |
| Phosphine Conc., mM | 310 | 1000 |
| 1-Butene Feed, mole/hr/L | 4.0 | 2.8 |
| Aldehyde Product, mole/hr/L | 1.0 | 2.3 |
| Conversion per Pass % | 26 | 82 |
|  |  | 6.5* |
| n + i Selectivity % | 92 | 84 |
| n/i ratio | 21 | 29 |
| Hydrocarbon Selectivity, % (and Other By-Products) | 7 | 14 |
| Stripping Gas, mole/hr/L | 35 | 21 |

*After 6 days operation.

Surprisingly, they formed monohydric alcohols and their carboxylic acid esters and acetals plus dimeric aldehyde condensation products rather than the trimeric and tetrameric adducts of the prior art. These higher boiling oxygenated solvent components became enriched in the reaction mixture during the six day continuous operation and appeared to reach a quasi equilibrium concentration.

The activity of the catalyst system was determined by periodically weighing the crude liquid aldehyde condensation product of the PFO operation. This contained about 85% n-valeraldehyde and about 10% of 1-butene. The 1-butene conversion and the $H_2$ and CO partial pressures in the reactor were determined on the basis of a material balance provided by analyzing all the components of the system. The data are listed in Table X. The results show that 1-butene feed conversion and aldehyde production was fully maintained for 160 hours.

The selectivity of the catalyst system was also analyzed and is shown in Table XI. The results show that both the total aldehyde percentage and the n/i aldehyde ratio remained essentially constant. The selectivity to hydrocarbon by-products in this run is high, due to the relatively low CO partial pressure (255 kPa, i.e., 37 psia).

After the completion of the PFO hydroformylation, the composition of the residual catalyst system was analyzed by gas chromatography. The approximate total weight of the system was about 500 g, indicating a highly efficient flash-off operation. Most of the mixture, about 87%, was of course triphenylphosphine. The valeraldehyde content was about 8%. The percentage of the amyl alcohol solvent component was about 3.5%. The amount of the higher boiling alcohols, aldehydes and carboxylic acid alkyl esters derived from the unsaturated aldol aldehyde intermediates was about 1.5%.

TABLE X

ACTIVITY MAINTENANCE IN THE CONTINUOUS PFO HYDROFORMYLATION OF 1-BUTENE WITH THE $Ph_3P$-RH CATALYST SYSTEM AT HIGH $Ph_3P$ CONCENTRATION

|  | 1 23 Hrs | 2 46 Hrs | 3 65 Hrs | 4 136 Hrs | 5 160 Hrs |
|---|---|---|---|---|---|
| Mole Balances, % |  |  |  |  |  |
| $H_2$ | 99 | 100 | 109 | 98 | 99 |
| CO | 92 | 95 | 101 | 96 | 93 |
| $C_4$ | 85 | 91 | 98 | 93 | 93 |
| Liquids, g/hr | 133 (16% Toluene) | 129 | 135 | 133 | 132 |
| Conversion (feed), % | 55 | 61 | 64 | 63 | 63 |
| $P_{H2}$, kPa | 917 | 917 | 917 | 903 | 917 |
| $P_{CO}$, kPa | 255 | 255 | 248 | 262 | 248 |

TABLE XI

SELECTIVITY MAINTENANCE IN THE CONTINUOUS HYDROFORMYLATION OF 1-BUTENE WITH THE $Ph_3P$-Rh CATALYST SYSTEM AT HIGH $Ph_3P$ CONCENTRATION

|  | 1 23 Hrs | 2 46 Hrs | 3 65 Hrs | 4 136 Hrs | 5 160 Hrs |
|---|---|---|---|---|---|
| Butane, % | 9 | 8 | 6 | 7 | 6 |
| 2-Butenes, % | 19 | 17 | 18 | 17 | 18 |
| Total Aldehyde, % | 69 | 74 | 72 | 74 | 74 |
| Aldehyde n/i | 33 | 37 | 33 | 32 | 31 |
| Alcohol, % | 3 | 2 | 4 | 3 | 3 |
| Alcohol n/i | 51 | — | 55 | 51 | 48 |

Only trace amounts of trimers were present (<0.1%). Thus the analyses shown that, in the present high temperature continuous hydroformylation a novel oxygenated solvent is formed which is surprisingly beneficial for maintaining the stability and selectivity of the catalyst system and facilitates an effective product flash-off.

The residual catalyst system contained only about 0.5% of n-butyldiphenylphosphine and n-pentyldiphenylphosphine degradation products of triphenylphosphine. The distillate product had in the range of 1-2 ppm of the same conversion products. Therefore, it is estimated that in a month operation only about 2.5-3% of the triphenylphosphine ligand is converted to alkyldiphenylphosphines. Also, some of the triphenylphosphine is flashed off, there is about 15 ppm $Ph_3P$ in the distillate product.

Example 87

Identification of the Oxygenated Solvent Components Formed in High Temperature Hydroformylation The oxygenated solvent components formed in the continuous process described in the previous example were studied by combined gas chromatography and mass spectroscopy. These GC/MS studies with the help of authentic compounds resulted in the structural identification of most of the components. The starting material for this work was a distillate product obtained during the second day of the PFO operation. The product was concentrated 62 fold by fractional distillation to remove the hydrocarbons and valeraldehydes. The remaining "heavies" were then analyzed by GC/MS.

The reconstructed ion chromatogram of the components is shown by FIG. 8, together with the identification of the major components. It is noted that n-pentanol constitutes about 56% of the oxygenates of this mixture. 2-Propylheptanal is second in amount with about 7%. The less volatile $C_{15}$ valeraldehydes diamyl acetal and the three isomeric $C_{15}$ monocarboxylic acid esters are smaller components in the range of 1%. Only traces of the isomeric trimers of the prior art were detected. None of the tetramer was found. Thus these studies showed the different character of the present system.

Example 88

Recovery of Triphenylphosphine Ligand and Its Rhodium Complex by Crystallization After the completion of the continuous PFO hydroformylation experiment of Example 85, the solution of the catalyst system was concentrated by distillation in vacuo using a bath temperature of up to 85° C. About 464 g distillation residue, predominantly containing excess triphenylphosphine ligand was obtained.

The above catalyst residue was extracted under nitrogen 4 times with about 1100 ml each of hot methanol. The resulting methanol solutions were allowed to cool to room temperature. Crystallization occurred on cooling. The crystals were separated by filtration with suction and dried at about 0.1 mm pressure at ambient temperature. The combined crystalline material was essentially triphenylphosphine and tris-triphenylphosphine rhodium monocarbonyl hydride. The rhodium content was about 500 ppm.

On the basis of its rhodium content the recovered material was found to be fully effective as a hydroformylation catalyst in a standard batch test at 145° C. Thus, the above method of recovery provides a crystalline mixture of catalyst systems component suitable for return to the continuous hydroformylation reactor.

Further methanol extraction resulted in a more complete catalyst recovery. However, the additional crystal crops had a decreasing rhodium content.

It was found that components of the above type catalyst system containing a high concentration of triphenylphosphine also crystallized on cooling without prior distillation and methanol addition.

Example 89

Continuous 2-Butene Hydroformylation at 140° C.

The concurrent isomerization hydroformylation of 2-butene was also studied in the continuous PFO reactor, without added trimer solvent and aldehyde recycle in a manner analogous to Example 85.

For the start, the reactor was charged with a warm toluene solution of 3.5 moles of triphenylphosphine and 0.1 moles of rhodium dicarbonyl acetonate.

During the first part of the study the reactor was run under a total pressure 1275 kPa (185 psia) at 140° C. in the manner described in Example 85. Initially, 36 g/hr crude liquid aldehyde product was produced. However, the rate of production decreased to about 25 g/hr in 114 hours. The n/i ratio of the aldehyde product was about 3.4 and remained about constant. The total aldehyde selectivity was low, about 53%. The main by-product was butane with a selectivity of 26%. The alcohol selectivity was also high, 8%; presumably due to the high rhodium concentration.

During the following 88 hour period of the study, the total pressure was doubled, the other operational parameters stayed the same. The increased pressure resulted in an increased aldehyde production rate, about 70 g/hr, and improved activity maintenance. The total aldehyde selectivity was also improved to about 65%. However, the n/i ratio dropped to 1.1, apparently due to the increased CO partial pressure.

What is claimed is:

1. A homogeneous liquid phase hydroformylation process which comprises reacting a dissolved olefin with CO and $H_2$ at temperatures between about 120° and 200° C. and at a total pressure in the range of 100 to 1500 psia to selectively produce aldehydes in the presence of tris-triarylphosphine rhodium monocarbonyl hydride and bis-triarylphosphine rhodium dicarbonyl hydride complex catalyst free from halogen on the rhodium wherein the homogeneous reaction medium comprises oxygenated solvents comprising mainly straight chain and branched monohydric alcohols and aliphatic monocarboxylic acid esters and aldehyde acetals thereof, and branched aldehydes derived via aldol condensation and excess triaryl phosphine ligand as catalyst stabilizer modifier having a minimum of 1 mole per kg. phosphorus equivalent based on said reaction medium wherein the daily loss of catalyst activity is below 0.5%.

2. The process of claim 1 wherein the oxygenated solvents are formed during the hydroformylation process.

3. The process of claim 1 wherein the olefin reactant is an unsymmetrical disubstituted ethylene and the CO partial pressure is above 60 psia.

4. The process of claim 1 wherein olefin reactant is a linear internal olefin.

5. The process of claim 1 wherein olefin reactant has a nonhydrocarbon substituent.

6. The process of claim 5 wherein the olefin reactant is allyl t-butyl ether.

7. The process of claim 1 wherein the CO partial pressure is between 25 and 500 psia.

8. A homogeneous liquid phase hydroformylation process which comprises selectively reacting a dissolved $C_2$-$C_{40}$ 1-n-olefin with CO and $H_2$ at temperatures between about 120° and 200° C. and at a total pressure of 100 to 1500 psia to selectively produce n-aldehydes in the presence of a tris-triarylphosphine rhodium carbonyl hydride complex catalyst free from halogen on the rhodium wherein the homogeneous reaction medium comprises oxygenated solvents comprising mainly straight chain and mono-branched monohydric alcohols and aliphatic mono carboxylic acid alkyl esters and aldehyde acetals thereof, and branched aldehydes derived via aldol condensation and excess triarylphosphine ligand as a catalyst stabilizer modifier having a minimum of 1 mole per kg. phosphorus equivalent based on said reaction medium wherein the daily loss of catalyst activity is below 0.5%.

9. The process of claim 8 wherein the 1-n olefin has a carbon range of 4 to 12.

10. The process of claim 8 wherein the 1-olefin reactant is part of a mixed olefinic feed.

11. The process of claim 8 wherein the triarylphosphine ligand is triphenylphosphine having a concentration ranging from 1 to 2.9 moles per kg. phosphorus equivalent.

12. The process of claim 8 wherein the ratio of $H_2$ to CO reactants is between 2.5 and 15.

13. A concurrent homogeneous isomerization, hydroformylation process comprising isomerizing an internal linear olefin to a terminal $C_4$–$C_{40}$ 1-n-olefin and hydroformylating the 1-olefin component resulting from the isomerization in the presence of a tris-triarylphosphine rhodium carbonyl hydride complex catalyst free from halogen on the rhodium wherein the homogeneous reaction medium comprises oxygenated solvents comprising mainly straight chain and mono-branched monohydric alcohols and monocarboxylic acid alkyl esters and aldehyde acetals thereof and branched aldehydes derived via aldol condensation and excess triarylphosphine ligand as a catalyst modifier stabilizer having a minimum of 1 mole per kg. phosphorus equivalent based on said reaction medium and wherein the CO partial pressure is below 100 psia.

14. The process of claim 13 wherein the internal olefin reactant is 2-butene.

15. A continuous homogeneous liquid phase hydroformylation process which comprises reacting a dissolved $C_2$ to $C_{12}$ olefinic feed with CO and $H_2$ at temperatures between about 120° and 200° C. and at a total pressure in the range of 100 to 1500 psia to selectively produce aldehydes in the presence of tris-triarylphosphine rhodium monocarbonyl hydride and bis-diarylphosphine rhodium dicarbonyl hydride complex catalyst free from halogen on the rhodium wherein homogeneous reaction medium comprise oxygenated solvents comprising mainly straight chain and mono-branched monohydric alcohols and aliphatic monocarboxylic acid alkyl esters and aldehyde acetals thereof and branched aldehydes derived via aldol condensation and excess triarylphosphine ligand as a catalyst modifier stabilizer having a minimum of 1 mole per kg. phosphorus equivalent based on said reaction medium wherein the daily loss of catalyst activity is below 0.5% and continuously removing the products and unreacted reactants in the gas phase.

16. The process of claim 15 wherein the olefin reactant is a linear internal olefin.

17. The process of claim 16 wherein the olefin reactant is 2-butene.

18. The process of claim 15 wherein the olefin reactant is an unsymmetrically disubstituted ethylene.

19. The process of claim 15 wherein the tris-triarylphosphine rhodium carbonyl hydride and the triarylphosphine are recovered from said medium by crystallization and returned to the reactor.

20. The process of claim 15 wherein the olefin reactant has a nonhydrocarbon substituent.

21. The process of claim 15 wherein $H_2$ and CO are recirculated in the substantial absence of product aldehyde.

22. A continuous homogeneous liquid phase hydroformylation process comprising reacting a $C_4$ to $C_{12}$ n-1 olefinic feed with CO and $H_2$ at temperatures between about 120° and 200° C. and at a total pressure of 100 to 1000 psia to selectively produce n-aldehydes in the presence of a tris-triarylphosphine rhodium carbonyl hydride complex catalyst free from halogen on the rhodium wherein said reaction medium comprises oxygenated solvents comprising mainly monohydric alcohols and mono carboxylic acid esters and acetals thereof and branched aldehydes and excess triaryl phosphine ligand as catalyst stabilizer modifier having 1 mole per kg. phosphorus equivalent based on said oxygenated solvent, continuously removing the products and unreacted reactants from said medium during the reaction in the gas phase, and recirculating $H_2$ and CO in the substantial absence of product aldehyde.

23. The process of claim 22 wherein the daily loss of catalyst activity is below 0.3%.

24. The process of claim 22 wherein the triarylphosphine is triphenylphosphine having a concentration ranging from 1 to 2.9 moles per kg. phosphorus equivalent.

25. The continuous PFO hydroformylation process of claim 22 wherein the CO partial pressure is between 25 and 500 psia.

26. The continuous process of claim 22 wherein the ratio of $H_2$ to CO reactants is between 2.5 and 15.

27. The continuous process of claim 22 wherein the 1-n olefin reactant is fed as a component of an olefinic mixture.

28. The continuous process of claim 22 wherein an alkyldiarylphosphine bis-triarylphosphine rhodium monocarbonyl hydride complex is also present in the reaction medium.

29. A continuous homogeneous liquid phase hydroformylation process which comprises reacting a dissolved butene-1 feed with CO and $H_2$ at temperatures between about 120° and 160° C., a total pressure in the range of 100 to 700 psia to selectively produce n-valeraldehyde in the presence of tris-triphenylphosphine rhodium carbonyl hydride complex catalyst free from halogen on the rhodium wherein the homogeneous reaction medium comprises oxygenated solvents containing amyl alcohol, amyl propylheptanoate, valeraldehyde diamyl acetal, propylheptanal, propylheptanol, and excess triarylphosphine ligand having a minimum of 1 mole per kg. phosphorus equivalent based on said reaction medium and wherein the daily loss of catalyst activity is below 0.5%, continuously introducing reactants into the liquid reaction medium, continuously removing aldehyde products and unreacted reactants in the gas phase, separating the products by condensation and recirculating $H_2$ and CO in the substantial absence of aldehyde product.

30. A continuous homogeneous liquid phase hydroformylation process comprising reacting a $C_4$ to $C_{12}$ linear internal olefinic feed with CO and $H_2$ at temperatures between about 120° and 200° C. and at a CO partial pressure above 100 psi and a total pressure not exceeding 1500 psia to selectively produce aldehydes in the presence of a bis-triarylphosphine rhodium dicarbonyl hydride complex catalyst free from halogen on the rhodium wherein the homogeneous reaction medium comprises oxygenated solvents comprising mainly straight chain and mono-branched monohydric alcohols and aliphatic monocarboxylic acid alkyl esters and aldehyde acetals and branched aldehydes which oxygenated solvents are derived via aldol condensation in said reaction medium and excess triarylphosphine ligand as catalyst stabilizer modifier having a minimum of 1 mole phosphorus equivalent per kg. of reaction medium and continuously removing the products and unreacted reactants in the gas phase.

31. The process of claim 30 wherein said olefinic feed contains 2-butene as a reactant.

32. A continuous homogeneous liquid phase hydroformylation process which comprises reacting a $C_4$ to $C_{12}$ olefinic feed comprising one or more unsymmetrically disubstituted ethylene reactants with CO and $H_2$ at temperatures between about 120° and 200° C. and at a CO partial pressure in excess of 100 psia and a total pressure not exceeding 1500 psia to selectively produce terminal aldehydes in the presence of a bis-triarylphosphine rhodium dicarbonyl hydride complexed catalyst free from halogen on the rhodium wherein the homogeneous reaction medium comprises lower boiling oxygenated solvents comprising mainly straight chain and mono-branched monohydric alcohols and aliphatic mono-carboxylic acid alkyl esters and aldehyde acetals and branched aldehydes which oxygenated solvents are derived via aldol condensation in said reaction medium and excess triarylphosphine ligand as a catalyst stabilizer modifier having a minimum of 1 mole phosphorus equivalent per kg. of reaction medium.

33. The process of claim 32 wherein said olefinic feed comprises 2-ethylhexene as reactant.

34. The process of claim 32 wherein said olefinic feed comprises allyl t-butyl ether.

* * * * *